United States Patent
Ahamed

(10) Patent No.: US 11,752,122 B2
(45) Date of Patent: Sep. 12, 2023

(54) N-ACETYLCYSTEINE ATTENUATES AORTIC STENOSIS PROGRESSION BY INHIBITING SHEAR-MEDIATED TGF-BETA ACTIVATION AND SIGNALING

(71) Applicant: OKLAHOMA MEDICAL RESEARCH FOUNDATION, Oklahoma City, OK (US)

(72) Inventor: Jasimuddin Ahamed, Edmond, OK (US)

(73) Assignee: Oklahoma Medical Research Foundation, Oklahoma City, OK (US)

( * ) Notice: Subject to any disclaimer, the term of this patent is extended or adjusted under 35 U.S.C. 154(b) by 0 days.

(21) Appl. No.: 15/733,422

(22) PCT Filed: Feb. 1, 2019

(86) PCT No.: PCT/US2019/016231
§ 371 (c)(1),
(2) Date: Jul. 24, 2020

(87) PCT Pub. No.: WO2019/152765
PCT Pub. Date: Aug. 8, 2019

(65) Prior Publication Data
US 2021/0093599 A1 Apr. 1, 2021

Related U.S. Application Data

(60) Provisional application No. 62/625,652, filed on Feb. 2, 2018.

(51) Int. Cl.
| | | |
|---|---|---|
| *A61K 31/198* | (2006.01) | |
| *A61P 9/00* | (2006.01) | |
| *A61B 17/00* | (2006.01) | |
| *A61K 45/06* | (2006.01) | |

(52) U.S. Cl.
CPC ............ *A61K 31/198* (2013.01); *A61B 17/00* (2013.01); *A61K 45/06* (2013.01); *A61P 9/00* (2018.01); *A61B 2017/00243* (2013.01); *A61B 2017/00783* (2013.01)

(58) Field of Classification Search
None
See application file for complete search history.

(56) References Cited

U.S. PATENT DOCUMENTS

| | | | | |
|---|---|---|---|---|
| 2004/0131500 A1* | 7/2004 | Chow | ................. | G01N 11/14 422/72 |
| 2009/0069789 A1* | 3/2009 | Freyman | ................. | A61P 9/00 604/509 |
| 2010/0004248 A1 | 1/2010 | Kass et al. | | |
| 2015/0328235 A1* | 11/2015 | Miller | ................. | A61K 31/416 514/158 |

OTHER PUBLICATIONS

Foltz et al. "N-acetylcysteine prevents electrical remodeling and attenuates cellular hypertrophy in epicardial myocytes of rats with ascending aortic stenosis," Basic Res Cardiol (2012) 107:290. (Year: 2012).*
Reyes et al. "N-Acetylcysteine Influence on Oxidative Stress and Cardiac Remodeling in Rats During Transition from Compensated Left Ventricular Hypertrophy to Heart Failure," Cell Physiol Biochem 2017; 44:2310-2321. (Year: 2017).*
Wang et al. "Association Between Shear Stress and Platelet-Derived Transforming Growth Factor-β1 Release and Activation in Animal Models of Aortic Valve Stenosis," Arterioscler Thromb Vasc Biol Sep. 2014. (Year: 2014).*
Liberman et al. "Oxidant Generation Predominates Around Calcifying Foci and Enhances Progression of Aortic Valve Calcification," Arterioscler Thromb Vasc Biol 2008 (Year: 2008).*
Ahamed et al., "In vitro and in vivo evidence for shear-induced activation of latent transforming growth factor-β1," *Blood*, 112(9):3650-3660, 2008.
Mancini et al., "New methodologies to accurately assess circulating active transforming growth factor-β1 levels: implications for evaluating heart failure and the impact of left ventricular assist devices," *Translational Research*, 192:15-29, 2017.
Marenzi et al., "N-acetylcysteine and contrast-induced nephropathy in primary angioplasty," *N. Engl. J. Med.*, 354:2773-2782, 2006.
PCT International Search Report and Written Opinion issued in International Application No. PCT/US2019/016231, dated Apr. 24, 2019.
Reyes et al., "N-Acetylcysteine Influence on Oxidative Stress and Cardiac Remodeling in Rats During Transition from Compensated Left Ventricular Hypertrophy to Heart Failure," *Cellular Physiology and Biochemistry*, 44:2310-2321, 2017.
Smilkstein et al., "Efficacy of oral N-acetylcysteine in the treatment of acetaminophen overdose. Analysis of the national multicenter study (1976 to 1985)," *N. Engl. J. Med.*, 319(24):1557-1562, 1988.
Varga and Pasche, "Antitransforming growth factor-beta therapy in fibrosis: recent progress and implications for systemic sclerosis," *Curr Opin Rheumatol.*, 20(6):720-728, 2008.
Varshney et al., "Abstract 19231: N-acetylcysteine Inhibits Aortic Stenosis Progression in a Preclinical Murine Model: Role of Platelet TGF-β1," *Circulation*, 136(Suppl. 1):A19231, 2017.
Wang et al., "Association between shear stress and platelet-derived transforming growth factor-β1 release and activation in animal models of aortic valve stenosis," *Arterioscler. Thromb. Vasc. Biol.*, 34(9):1924-1932, 2014.
Weiss et al., "Calcific Aortic Valve Stenosis in Old Hypercholesterolemic Mice," *Circulation*, 114(19):2065-2069, 2006.
Yeang et al., "Experimental Animal Models Evaluating the Causal Role of Lipoprotein(a) in Atherosclerosis and Aortic Stenosis," *Cardiovasc Drugs Ther.*, 30(1):75-85, 2016.

* cited by examiner

*Primary Examiner* — Jeffrey S Lundgren
*Assistant Examiner* — Michael J Schmitt
(74) *Attorney, Agent, or Firm* — ParkerHighlander PLLC

(57) ABSTRACT

The present disclosure relates to compositions of N-acetylcysteine for use in treating aortic stenosis. Methods of treating aortic stenosis in a subject comprising administering to said subject an effective amount of N-acetylecysteine (NAC) or other thiol-reactive compound, or agents that inhibit TGF-Beta activation and/or signaling.

18 Claims, 24 Drawing Sheets
(20 of 24 Drawing Sheet(s) Filed in Color)

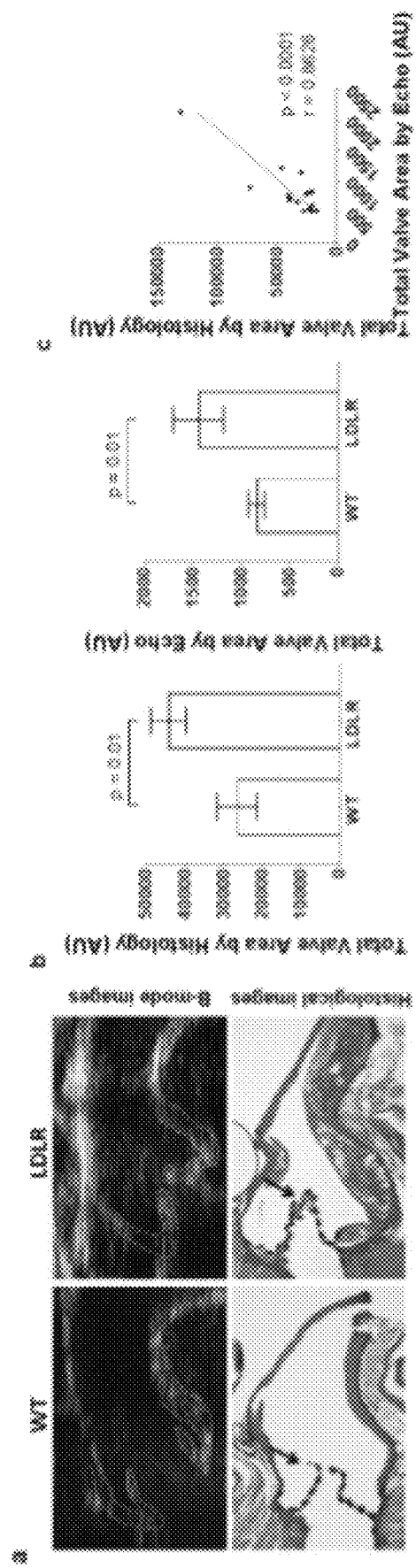
FIGS. 1A-C

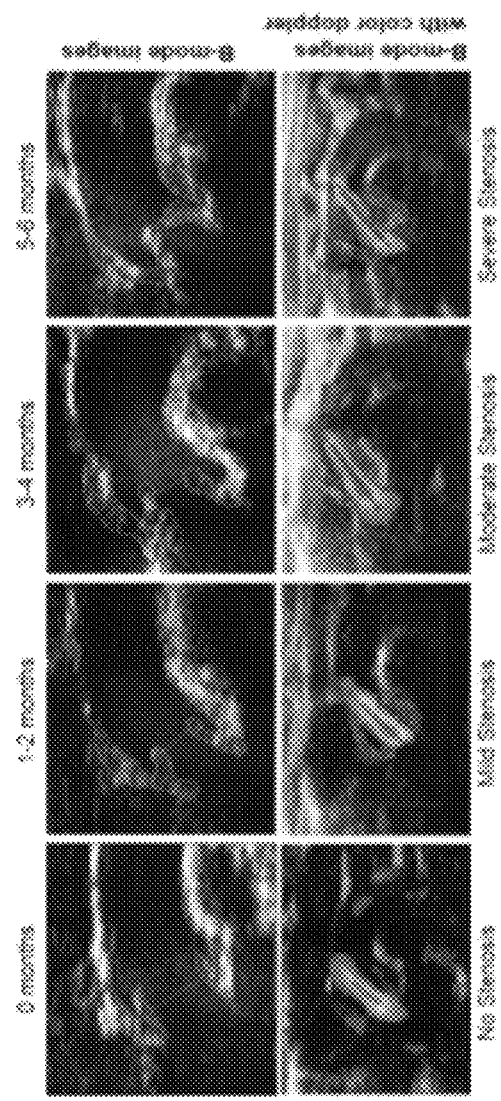
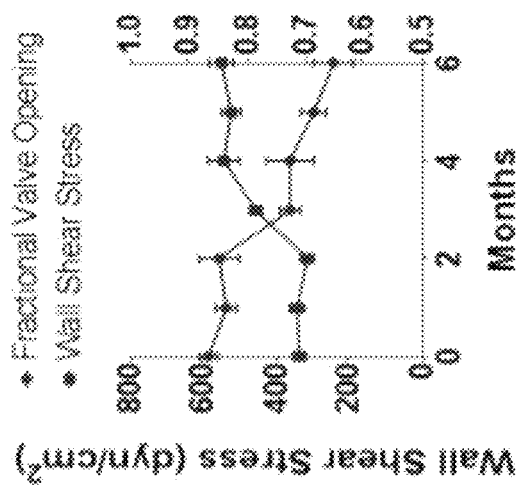
FIGS. 1D-E

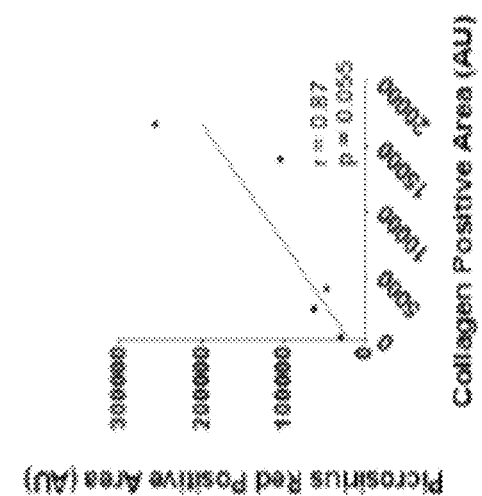
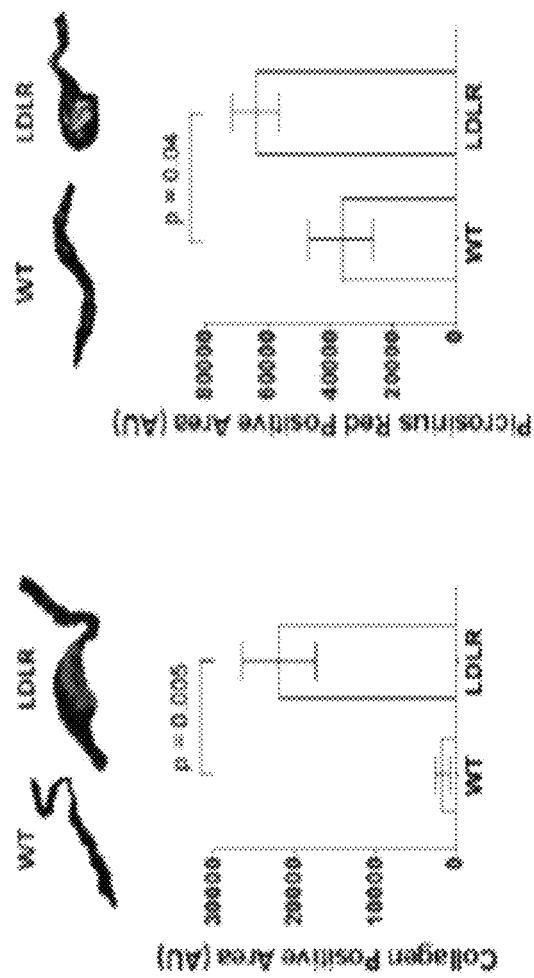
FIG. 1F

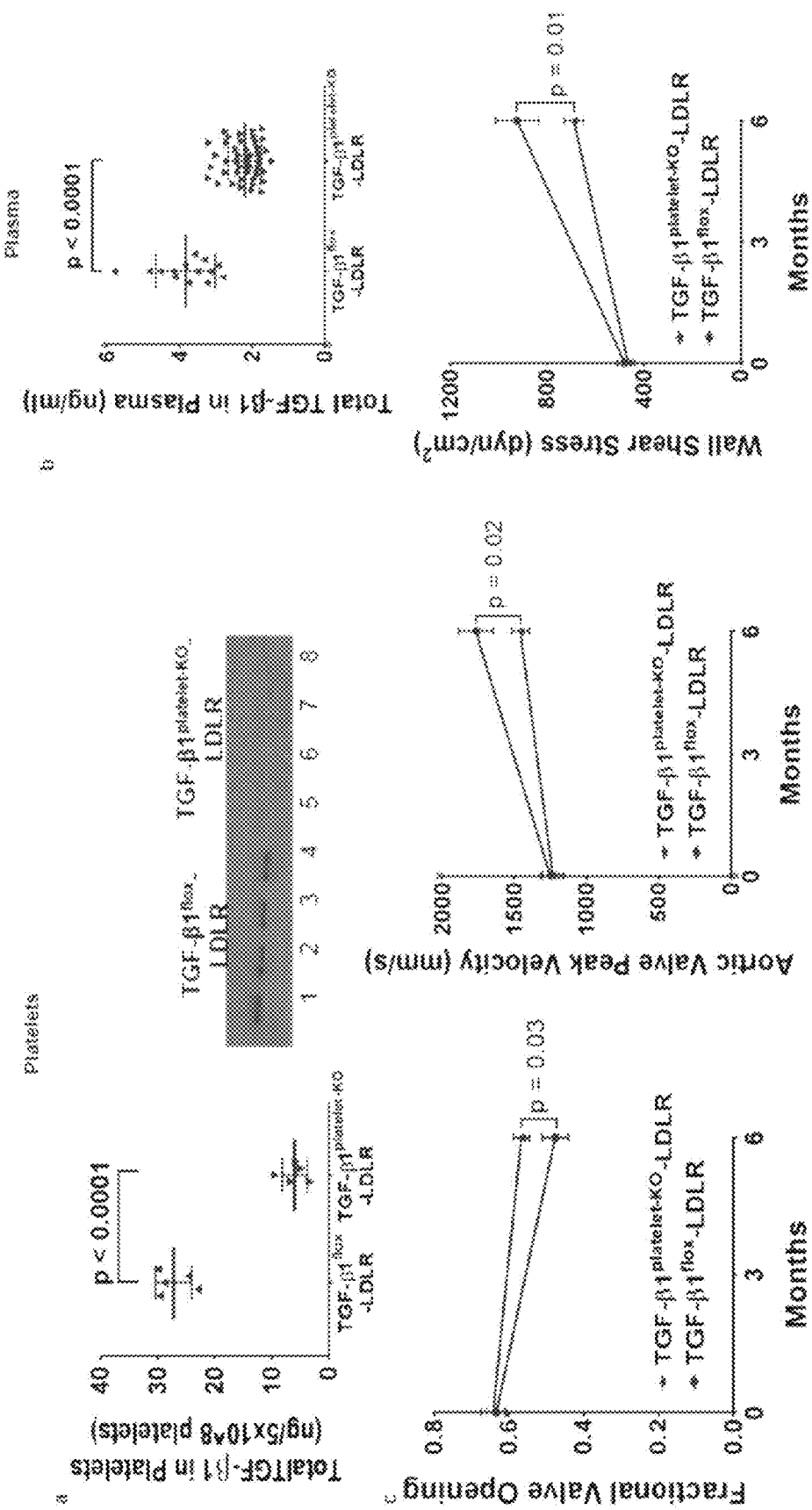
FIGS. 2A-C

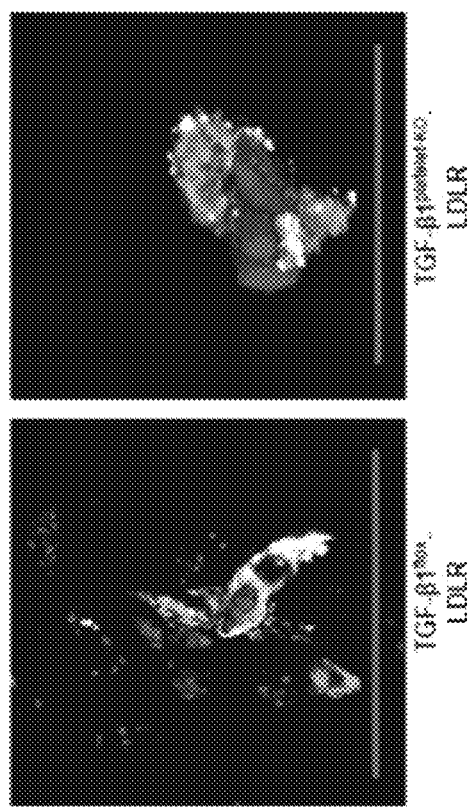
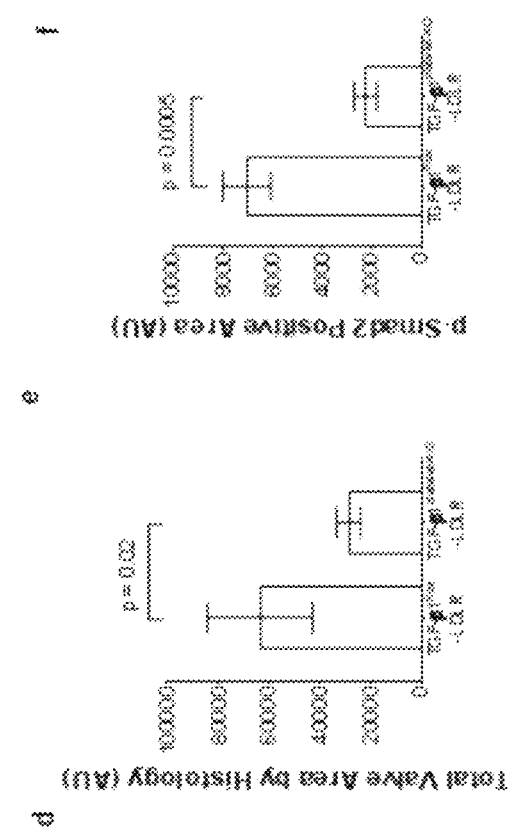
FIGS. 2D-F

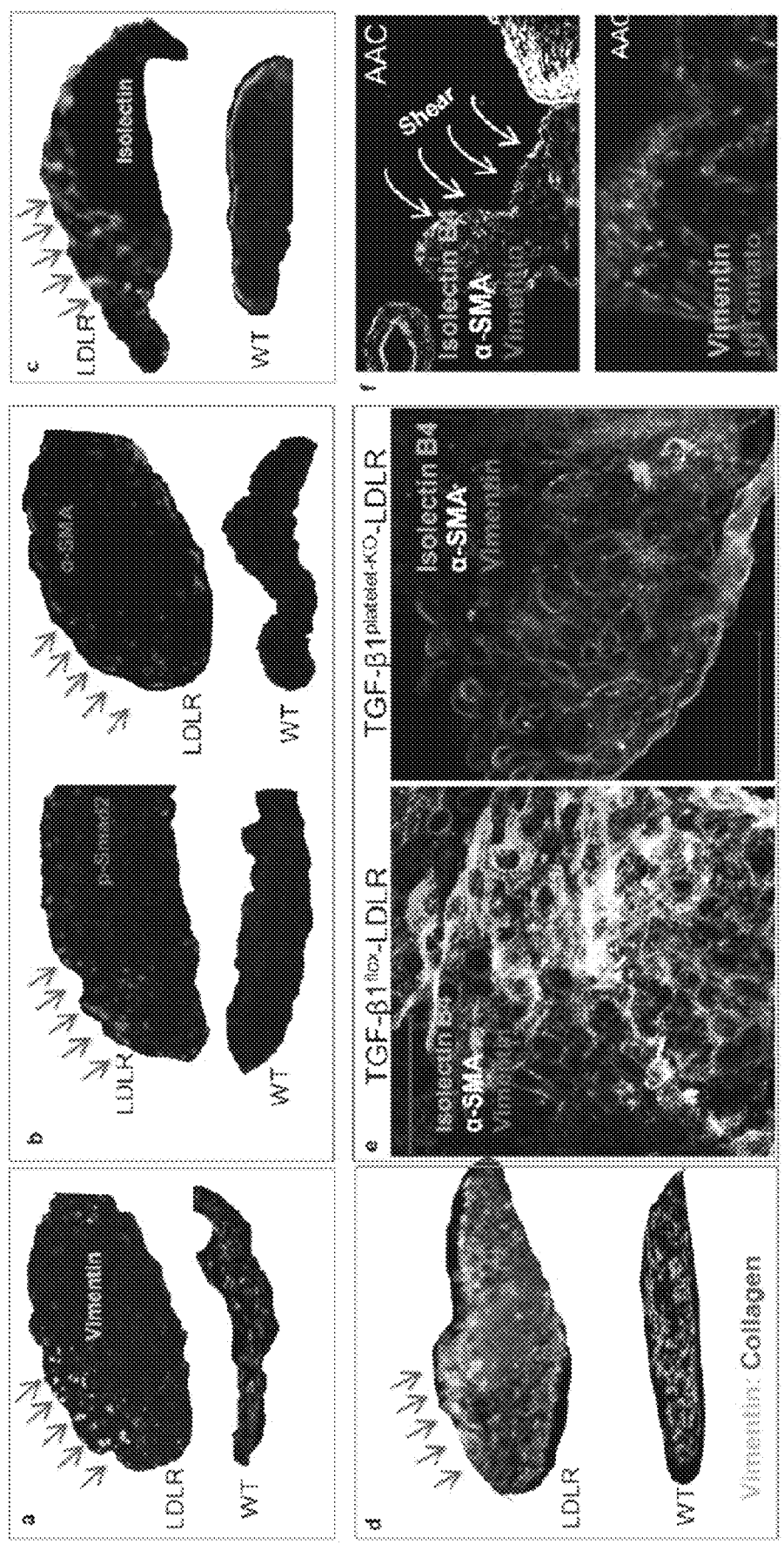
FIGS. 3A-F

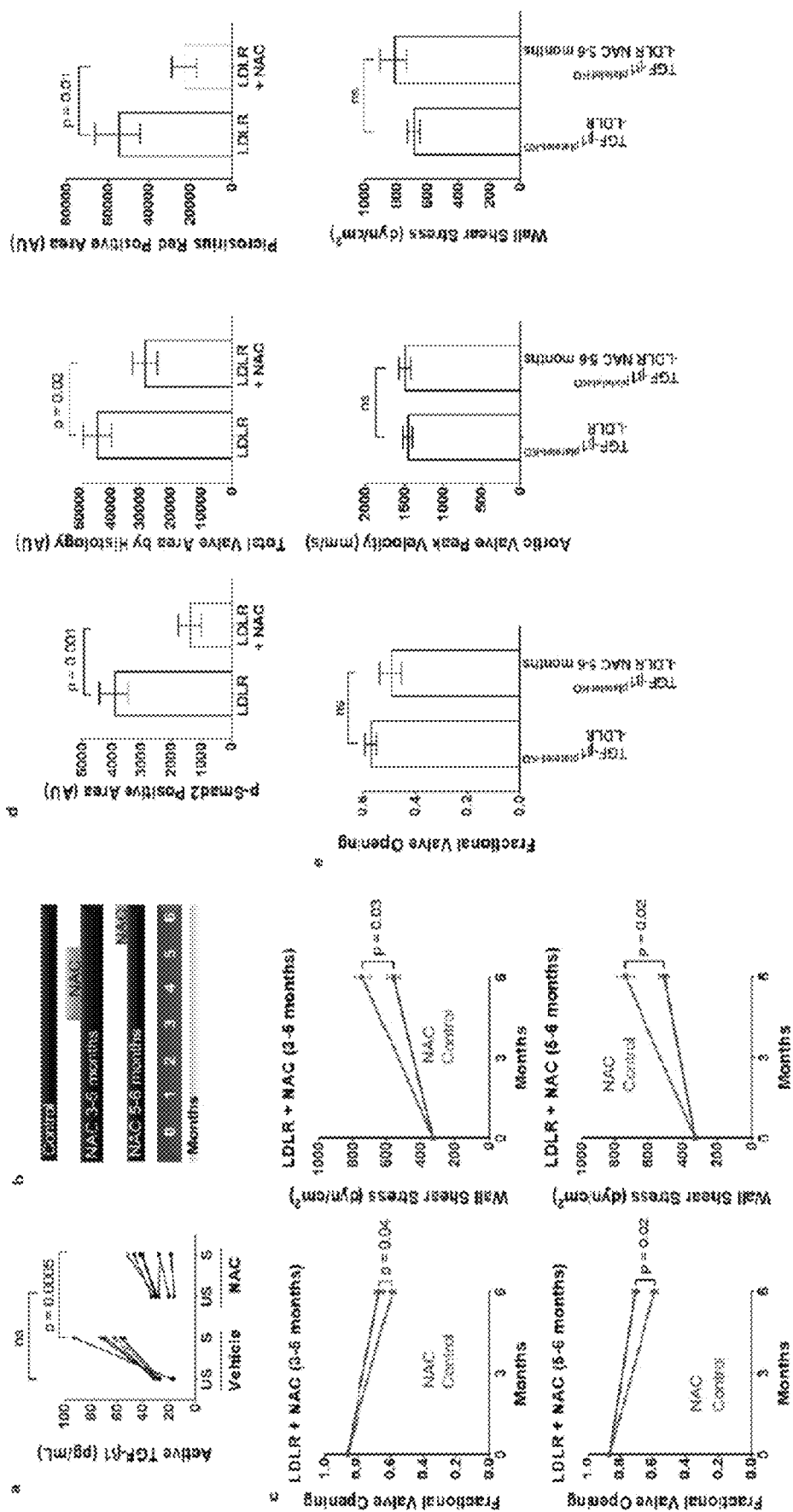
FIGS. 4A-E

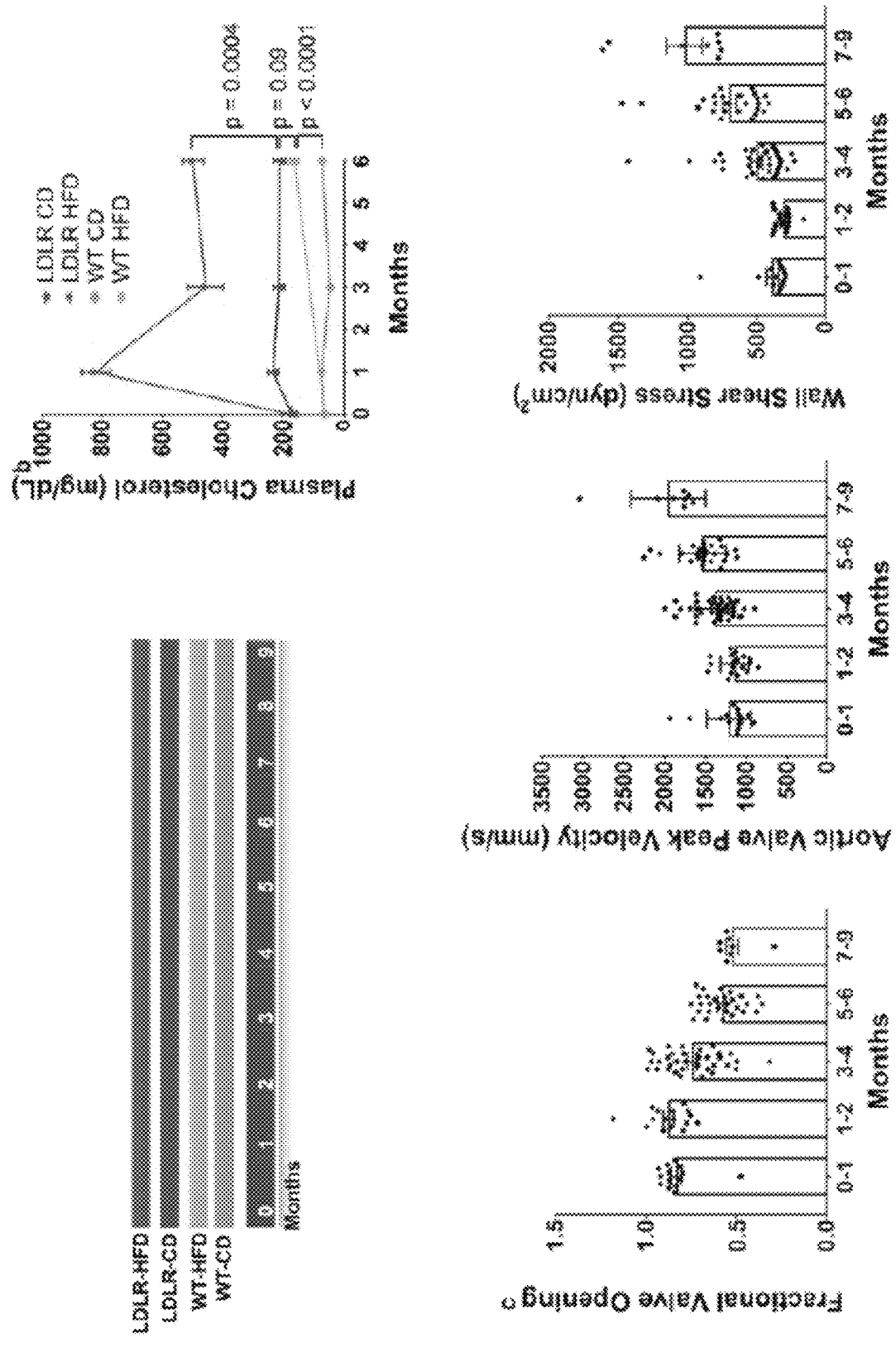
FIGS. 5A-C

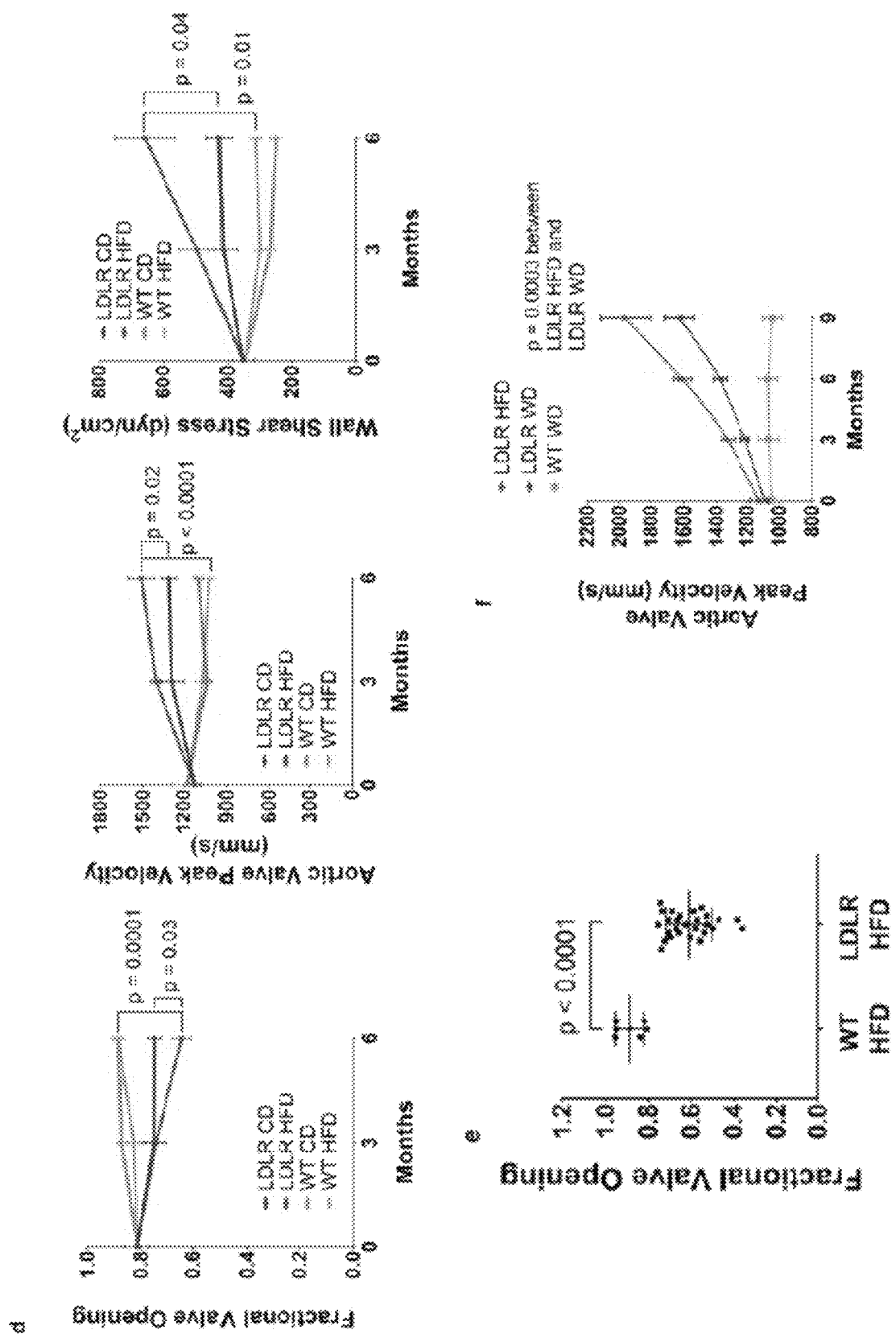
FIGS. 5D-F

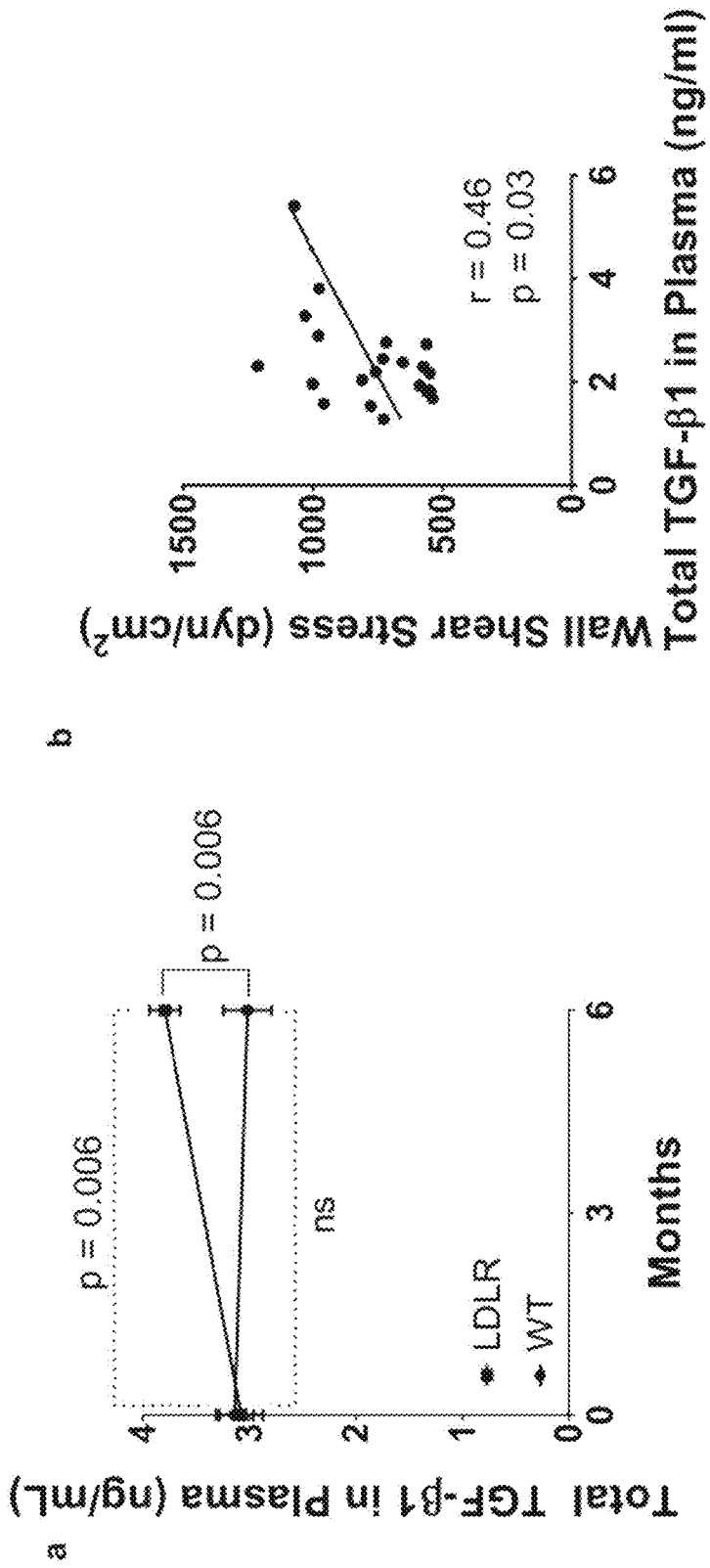
FIGS. 6A-B

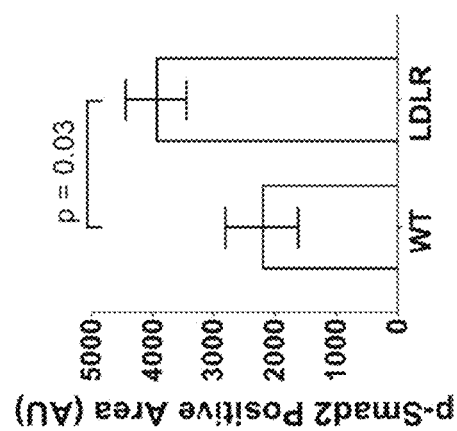
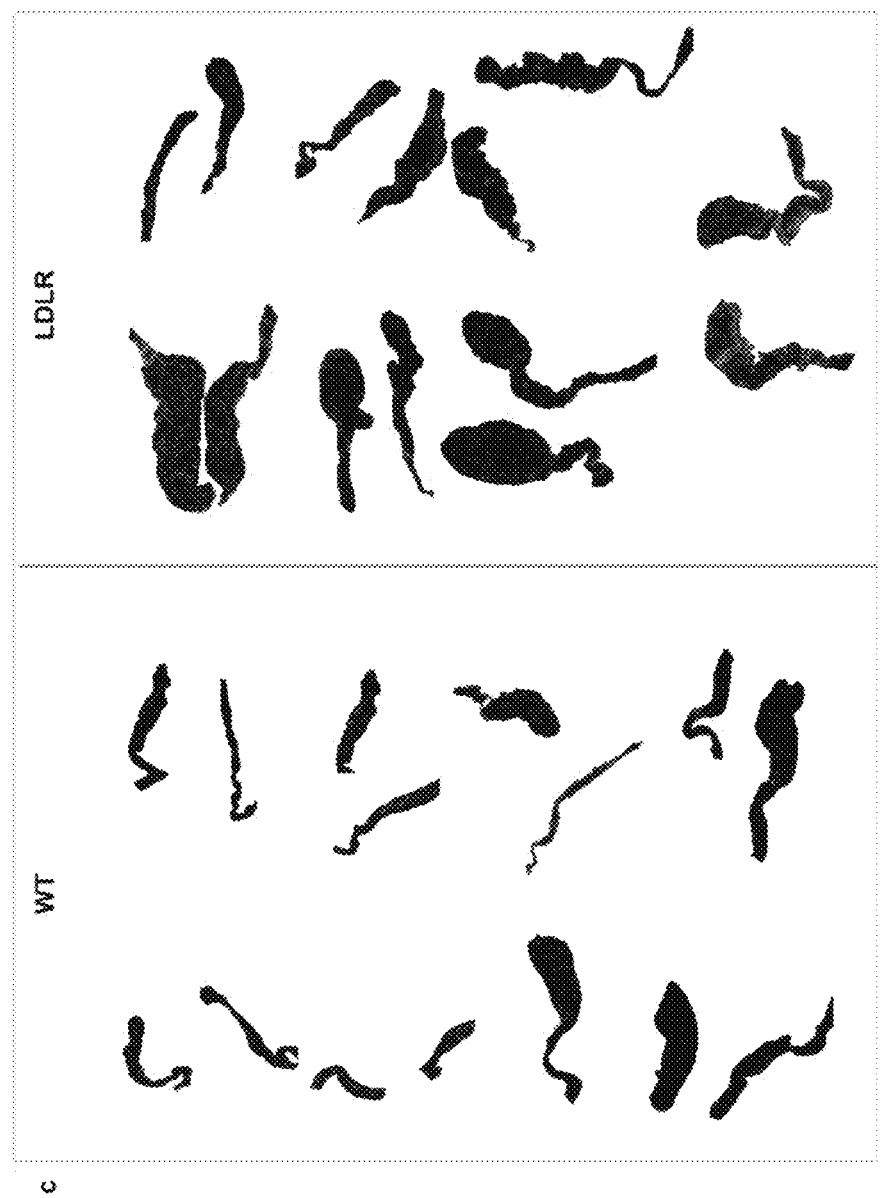
FIGS. 6C-D

Punnett Square for all heterozygous crossing.
Pf4Cre$^{+/-}$Tgfb1$^{f/+}$;Ldlr$^{-/+}$ApoB$^{+/-}$

FIG. 7B

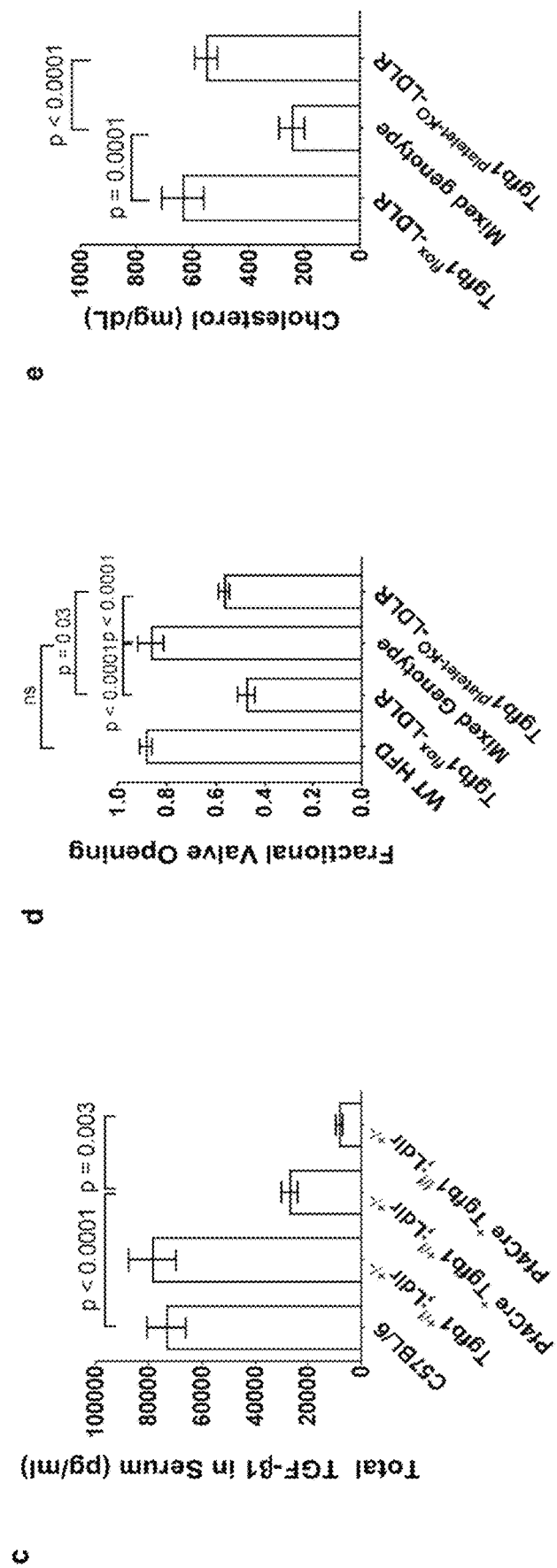
FIGS. 7C-E

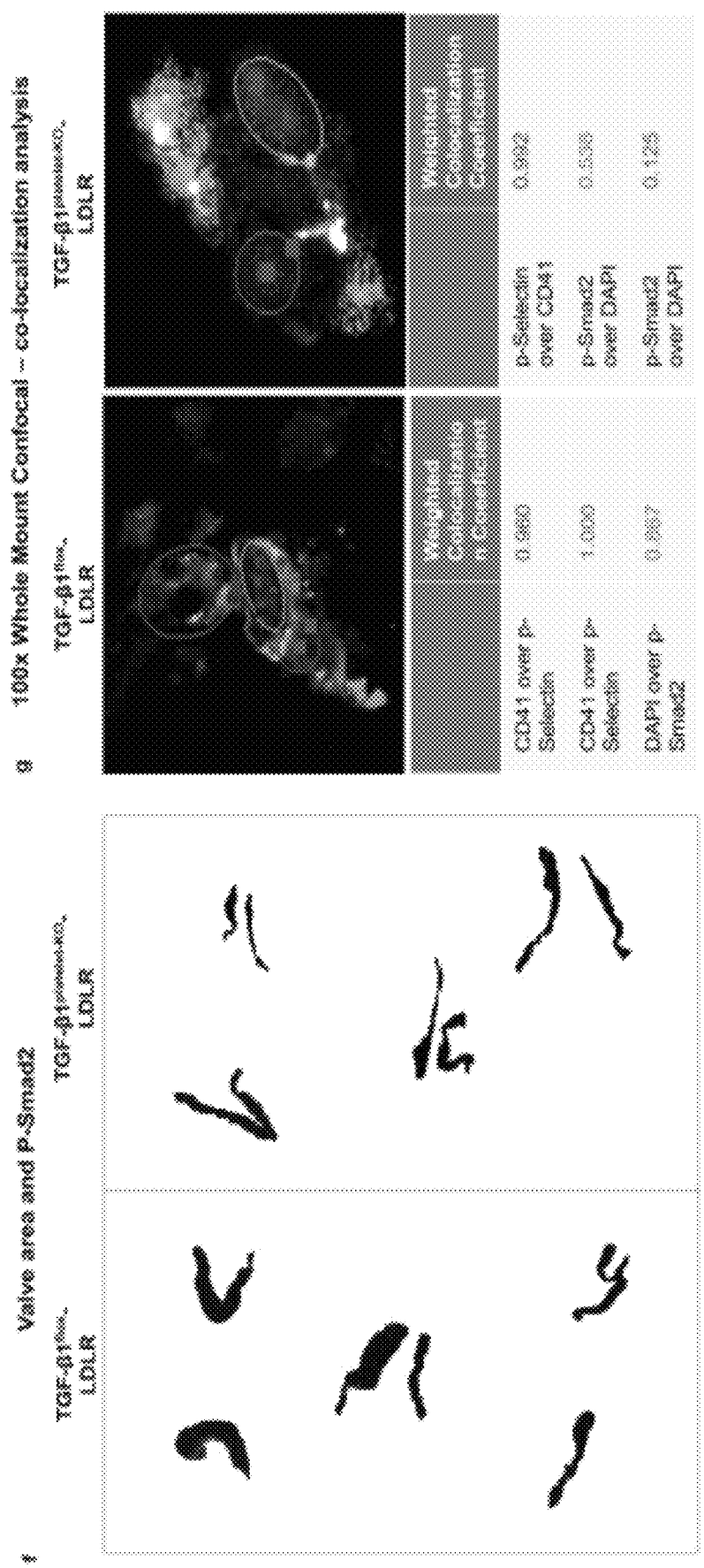
FIGS. 7F-G

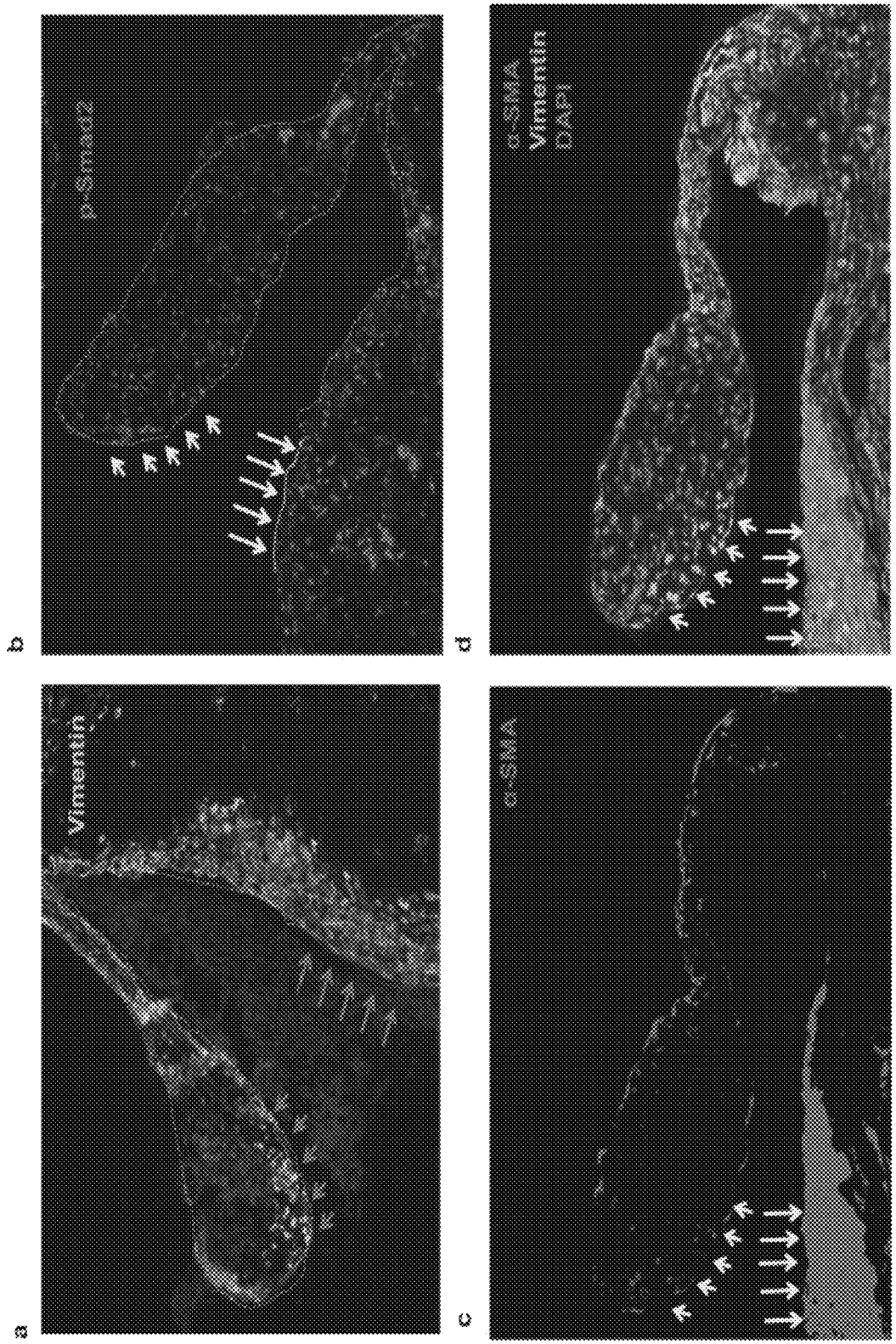
FIGS. 8A-D

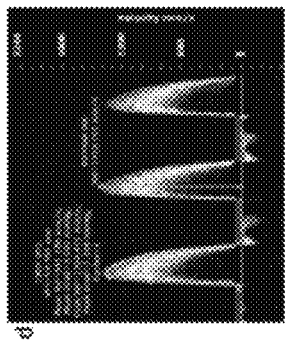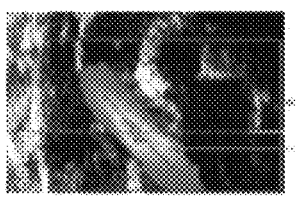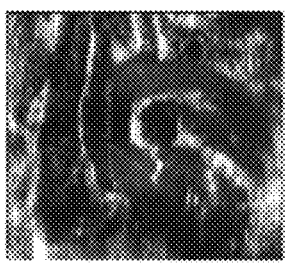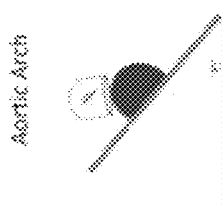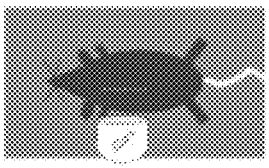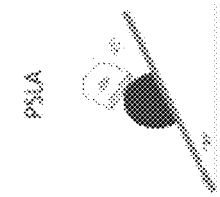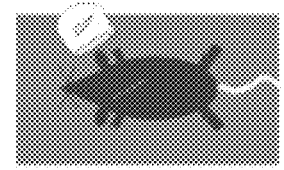
FIGS. 10A-F $EF = 100 \times LV\ Vol;d - LV\ Vol;s/LV\ Vol;d$
$FS = 100 \times LVID;d - LVID;s/LVID;d$
$SV = LV\ Vol;d - LV\ Vol;s$
$CO = (LV\ Vol;d - LV\ Vol;s) \times HR$
- LV Vol – left ventricle volume
- LVID – left ventricular internal diameter
- EF – ejection fraction
- FS – fractional shortening
- SV – stroke volume
- CO – cardiac output
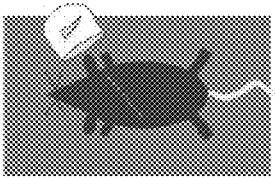
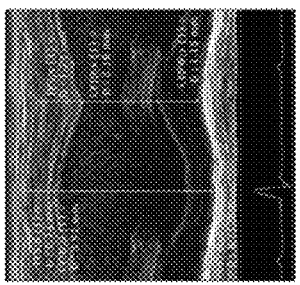
FIGS. 11A–C
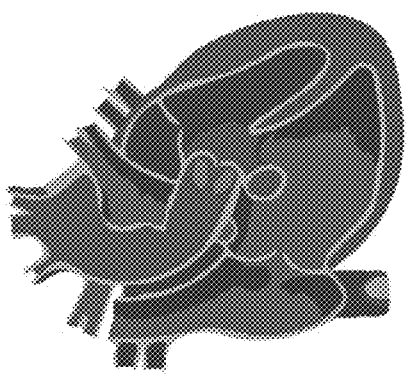
FIG. 12

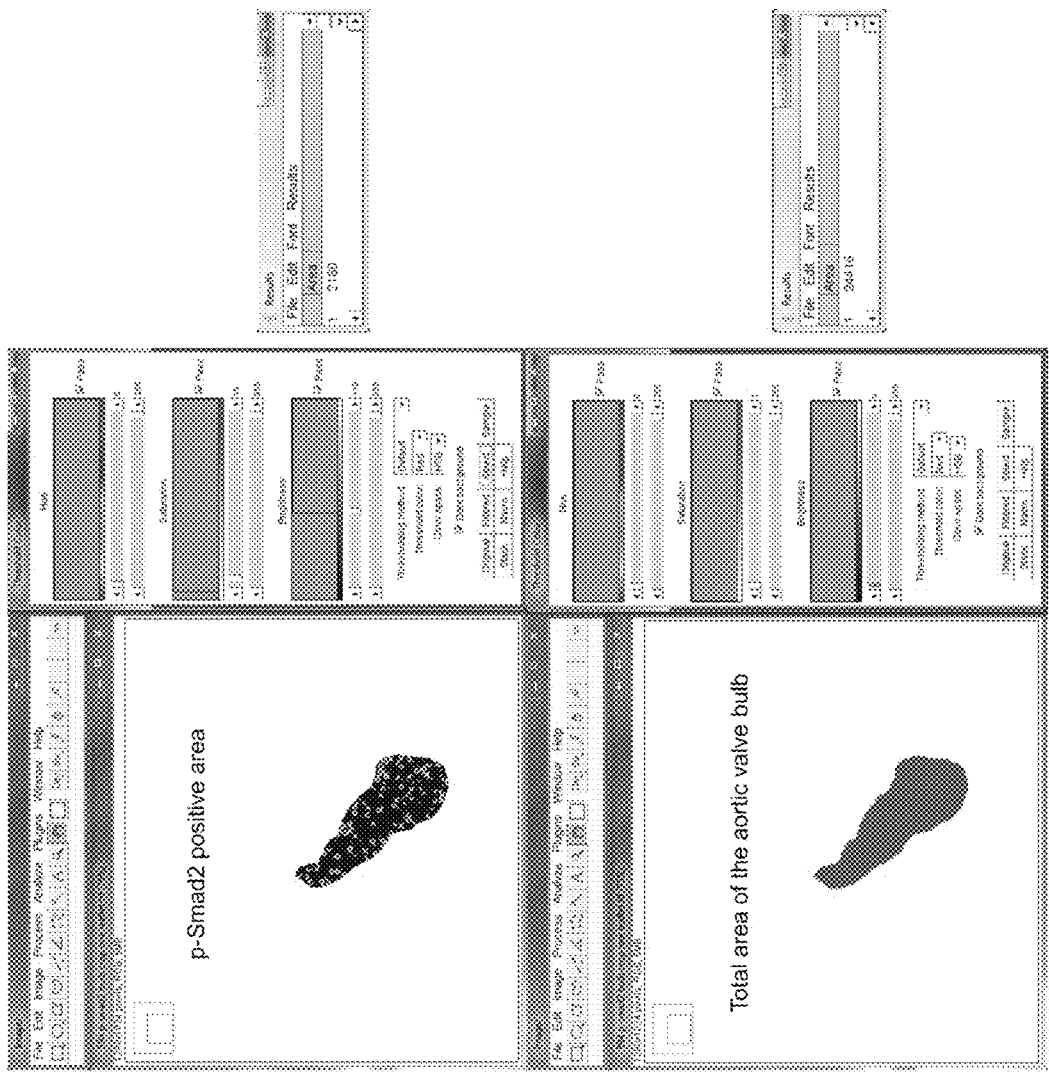
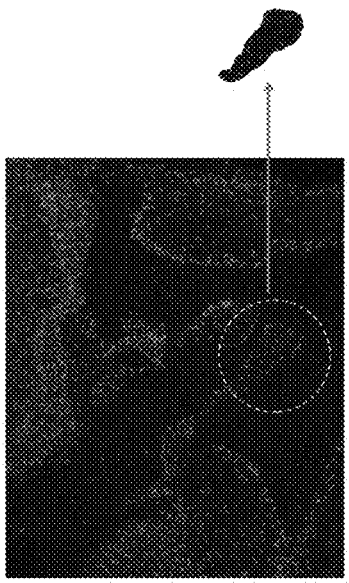
FIG. 13

N-ACETYLCYSTEINE ATTENUATES AORTIC STENOSIS PROGRESSION BY INHIBITING SHEAR-MEDIATED TGF-BETA ACTIVATION AND SIGNALING

PRIORITY CLAIM

This application is a national phase application under 35 U.S.C. § 371 of International Application No. PCT/US2019/016231, filed Feb. 1, 2019, which claims benefit of priority to U.S. Provisional Application Ser. No. 62/625,652, filed Feb. 2, 2018, the entire contents of each of which are hereby incorporated by reference.

The invention was made with government support under grant no. R01 HL123605 and grant no. R01 HL148123 awarded by the National Institutes of Health. The government has certain rights to this invention.

BACKGROUND

1. Field

The present disclosure relates generally to the fields of cardiology, hemostasis and thrombosis, fibrosis, developmental biology, biochemistry, and molecular biology. More specifically the use of pharmacologic compositions containing N-aceytlcystein to treat or inhibit the progression of aortic stenosis.

2. Description of Related Art

Aortic stenosis (AS), like other degenerative diseases, is characterized by increased fibrosis, calcification, and narrowing of aortic valves, resulting in high wall shear stress (WSS) across the valve (Rajamannan et al., 2011). AS primarily affects people over 65 years of age, and the only treatment available is valve replacement (Lindman et al., 2014). High levels of TGF-β1 in plasma have been observed in cardiac pressure-overload and AS mouse models (Meyer et al., 2012; Wang et al., 2014), and in patients with AS (Villar et al., 2009). Almost all cell types in the body can produce and secrete TGF-β1 in its latent form and platelets are a rich source of latent TGF-β1, containing 40 to 100 times more than other cell types, TGF-β1 is a remarkably potent cytokines when activated, but the mechanism of in vivo activation is not clear. The inventors discovered that WSS can activate latent TGF-β1 activation by 20-40-fold in in vitro assays (Ahamed et al., 2008).

A major challenge in drug development for AS is the lack of sufficiently robust preclinical animal models. Hyperlipidemic, and atherosclerotic mutant mouse models (Hajj et al., 2015; Sung et al., 2016; Chu et al., 2016; Jung et al., 2015; Bouchareb et al., 2015; Le Quang et al., 2014; Wang et al., 2014; Miller et al., 2010; Miller et al., 2009; Weiss et al., 2013; Chu et al., 2013 and Weiss et al., 2006) do not adequately simulate human AS pathology, with the possible exception of "LDL receptor-deficient and ApoB100-only" (Ldlr(−/−) Apob(100/100); LDLR) mice (Weiss et al., 2006; Yeang et al., 2016). Thus, more relevant and robust animal models are needed to permit the identification of new therapeutic interventions for the treatment of AS and other fibrotic diseases.

SUMMARY

Thus, in accordance with the present disclosure, there is provided a method of treating aortic stenosis in a subject comprising administering to said subject an effective amount of N-acetylecysteine (NAC) or other thiol-reactive compound, or agents that inhibit TGF-β activation and/or signaling. The subject may be a non-human mammal or a human. Administering may comprise oral administration, subcutaneous, intravenous administration, or inhalation. An effective amount may comprise about 0.01 to 4 g/kg/day. Treating may comprise slowing, mitigating or preventing the progression of said aortic valve stenosis.

The AS may be caused by age-related progressive fibrosis, calcification of a congenital bicuspid aortic valve unicaspid valves with unknown causes, acute rheumatic fever, post-inflammatory responses, Fabry disease, systemic lupus erythematosus, Paget disease, high blood uric acid levels, infection, mixed aortic valve diseases, including aortic regurgitation and aortic valve fusion after left ventricular assist device (LVAD) implantation in heart failure patients, and hypertension-induced cardiac pressure overload-induced heart failure and valvular disease.

The method may further comprise treating said subject with a statin or other cholesterol reducing agent, such as, statins, PCSK9 inhibitor, an anti-diabetic medication, such as metformin, an anti-hypertensive agent, such as a beta-blocker, a calcium blocker, a nitrate, digoxin, a diuretic, an ACE inhibitor, a thiol-reactive compounds, such as OKN007, an anti-oxidant, such as an Nrf2/HO-1 enhancer, a ROS scavenger, or an anti-inflammatory agent, such as anti-IL1β, anti-TNFα. The method may further comprise treating said subject with aortic valve repair, reconstruction or replacement surgically or percutaneously (TAVR/TAVI).

The compound may be administered daily, every other day, weekly, biweekly or monthly. These regimens may be applied to mild, moderate or severe disease states. Administration of said N-acetylecysteine (NAC) or other thiol-reactive compound may result in one or more of blocking platelet reactivity, blocking release and activation of factors responsible for inducing aortic stenosis.

The method may further comprise measuring platelet activation and release of factors, such as latent form of TGF-β1, its activation and their signaling components as biomarkers for predicting different stages of aortic stenosis or procoagulant stages in humans where high shear force (hemodynamix of blood flow pattern change in the vasculature, mechanical stain in tissues/cells) is observed. The subject may suffer from a fibrotic disease of the heart, lungs, kidney, liver or skin. The method may further comprising evaluating disease progression concurrent with time of treatment and the stage of disease (pathological fibrosis/calcification).

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present disclosure. The disclosure may be better understood by reference to one or more of these drawings in combination with the detailed description of specific embodiments presented herein.

FIGS. 1A-G. Development of a robust and aggressive mouse model of aortic stenosis (AS). (FIG. 1A) Ultrasound B-mode images (upper panels) and histological pictures (lower panels) of aortic valves in WT and LDLR mice on HFD. Arrows indicate aortic valve leaflets. (FIG. 1B) Total valve area as measured from echocardiographic images (n=14 WT, n=9 LDLR) and from histological images (n=14 WT, n=19 LDLR) of aortic valves. (FIG. 1C) Pearson correlation of aortic valve areas measured from echocardiography and histology (r=0.8626, p<0.0001, n=16). (FIG. 1D) Fractional valve opening (right Y-axis) and wall shear stress (left Y-axis) in LDLR mice fed HFD at indicated time points (n=7 to 31). (FIG. 1E) Top panel: Ultrasound images of aortic valves from LDLR mice before receiving HFD and at different time points thereafter for up to 6 months. Bottom panel: Ultrasound B-mode images with color Doppler of blood flow through aortic valves in LDLR mice at indicated time points. (FIG. 1F) Top: Immunohistochemistry for alpha-1 type I collagen (n=4 WT, n=5 LDLR) and picrosirius red staining for collagen (n=8 WT, n=17 LDLR) in aortic valves from WT and LDLR mice after 6 months on HFD. Bottom: quantification of collagen staining in the valves. Pearson correlation of collagen positive area measured from immunohistochemical and picrosirius red-stained images of aortic valves in LDLR mice after 6 months on HFD (r=0.87, p=0.055, n=5). (FIG. 1G) Whole mount confocal (Maximum Intensity Projection) image showing activated platelets adjacent to valvular cells. Whole mount staining for CD41, CD62P, p-Smad2 and DAPI (upper left panel). SEM images of aortic valves (at 200×, 2000× and 25000× magnification) showing activated platelets on the valve surface (Upper right panel). Whole mount confocal staining (CD41, CD62P, p-Smad2 and DAPI) for activated platelets and corresponding SEM (valve surface) images of the same area (middle and lower panels). Scale bar (-) represents 50 µm. Data represented as mean±s.e.m throughout.

FIGS. 2A-F. Platelet TGF-β1 contributes to AS progression. (FIG. 2A) Western blot and ELISA for total platelet TGF-β1 in TGF-β1$^{platelet-KO}$-LDLR mice (n=5) and TGF-β1$^{flox}$-LDLR controls (n=5). Lanes 1, 2, 3 and 4 in the blot represent platelet releasates from TGF-β1$^{flox}$-LDLR controls, and lanes 5, 6, 7 and 8 represent platelet releasates from TGF-β1$^{platelet-KO}$-LDLR mice. (FIG. 2B) Total plasma TGF-β1 in TGF-β1$^{platelet-KO}$-LDLR mice (n=45) and TGF-β1$^{flox}$-LDLR controls (n=14). (FIG. 2C) AS parameters—fractional valve opening, aortic valve peak velocity, and wall shear stress in TGF-β1$^{platelet-KO}$-LDLR mice (n=15) and TGF-β1flox-LDLR controls (n=7) at 0 and 6 months on HFD, as measured by echocardiography. (FIG. 2D) Quantification of total valve area of aortic valves of TGF-β1platelet-KOLDLR mice (n=4) and TGF-β1flox-LDLR controls (n=3) at 6 months on HFD from immunohistochemical staining images. (FIG. 2E) Quantification of p-Smad2-positive area in the aortic valves of TGF-β1platelet-KO-LDLR mice (n=4) and TGF-β1flox-LDLR controls (n=3) at 6 months on HFD from immunohistochemical staining images. (FIG. 2F) Whole mount confocal (Maximum Intensity Projection) images showing activated platelets adjacent to valvular endothelial cells (VECs) in a TGF-β1platelet-KO-LDLR mouse and a TGF-β1flox-LDLR control. Whole mount staining done for CD41, CD62P, p-Smad2 and DAPI. Scale bar (-) represents 50 µm. Data represented as mean±s.e.m throughout. TGF-β1platelet-KO-LDLR—Pf4Cre+Tgfb1f/f;Ldlr−/−Apob100/100. Littermate TGF-β1flox-LDLR controls—Tgfb1f/f;Ldlr−/−Apob100/100.

FIGS. 3A-F. Aortic valvular endothelial cells (VECs) undergo mesenchymal transition (VECMT) to produce collagen. (FIGS. 3A-C) Valve sections from WT and LDLR mice fed with HFD for 6 months were stained with vimentin, pSmad2, α-SMA, or IsolectinB4. Red arrows indicate a subset of cells expressing high levels of these markers in LDLR mice. (FIG. 3D) Valve sections from WT and LDLR mice fed with HFD for 6 months were stained with vimentin and alpha-1 type I collagen. (FIG. 3E) Whole mount aortic valve staining with isolectinB4, vimentin, and α-SMA in littermate TGF-β1flox-LDLR control mice and TGF-β1platelet-KO-LDLR mice. Scale bar (-) represents 50 µm. (FIG. 3F) Whole mount aortic valve staining with isolectinB4, vimentin, and/or α-SMA as indicated in WT mice (upper panel) and Tie2Cre; tdTomato mice (lower panel) after AAC surgery. White arrows indicate directional shear.

FIGS. 4A-E. NAC attenuates stenosis progression by blocking activation of TGF-β1. (FIG. 4A) Active TGF-β1 levels in platelet-rich plasma from NAC-treated (n=6) and -untreated (n=8) mice after in vitro stirring for 2 hours at room temperature, as measured by ELISA. (FIG. 4B) Schematic depiction of the experimental design: LDLR mice were started on HFD diet at 6-8 weeks of age and treated with NAC at 3 months for a period of 2 months, or at 5 months for a period of 1 month on HFD. Blood was collected and echocardiographic scans were performed at 0 and 6 months. (FIG. 4C) Quantification of stenosis parameters—fractional valve opening and wall shear stress—in NAC-treated (n=7 to 11) and -untreated (n=13 to 30) LDLR mice at 0 and 6 months on HFD, as measured by echocardiography. (FIG. 4D) Quantification of p-Smad2-positive area, total valve area, and fibrosis in the aortic valves of NAC-treated (n=11) and -untreated (n=20) LDLR mice at 6 months on HFD, as measured from immunohistochemical staining images. (FIG. 4E) Quantification of stenosis parameters—fractional valve opening, wall shear stress, and aortic valve peak velocity—in NAC-treated (n=5) and -untreated (n=15) TGF-β1platelet-KO-LDLR mice at 6 months on HFD, as measured by echocardiography. Data represented as mean±s.e.m throughout.

FIGS. 5A-F. LDLR mice on HFD have significantly higher plasma cholesterol levels and significantly worse aortic stenosis compared to LDLR mice on WD or CD, or to WT mice on HFD, WD or CD. (FIG. 5A) Schematic illustrating the experimental design: LDLR and WT mice were started on HFD at 6-8 weeks of age, or continued on CD, for 6-9 months. Blood was collected and echocardiographic scans were performed at various time points up to 9 months on HFD or CD. (FIG. 5B) Plasma cholesterol levels in LDLR mice on HFD (n=8 to 12) or CD (n=4 to 8) and WT mice on HFD (n=8) or CD (n=6 to 8) at various time points. (FIG. 5C) Penetrance of aortic stenosis in LDLR mice on HFD at various time points from the initiation of HFD diet as measured by fractional valve opening, aortic valve peak velocity, and wall shear stress. (FIG. 5D) Stenosis parameters—fractional valve opening, aortic valve peak velocity, and wall shear stress—in LDLR mice on HFD (n=10 to 48) or CD (n=5 to 12), and WT mice on HFD (n=5 to 13) or CD (n=5 to 10) at 0, 3 and 6 months after initiation of HFD as measured by echocardiography. (FIG. 5E) Fractional valve opening in WT (0.81±0.02, n=13) and LDLR (0.59±0.02, n=30) mice fed HFD for 6 months. (FIG. 5F) Aortic valve peak velocity in LDLR mice on HFD or WD, and WT mice on WD as measured by echocardiography. Data represented as mean±s.e.m throughout.

FIGS. 6A-D. (FIG. 6A) Total TGF-β1 levels in the plasma of LDLR and WT mice at 0 and 6 months on HFD, as measured by ELISA. (FIG. 6B) Pearson correlation of wall shear stress across aortic valves and plasma TGF-β1 levels in LDLR mice at 6 months on HFD (r=0.4, p=0.01, n=35). (FIG. 6C) Immunohistochemical staining of p-Smad2-positive valvular cells in the aortic valves of WT and LDLR mice analyzed after 6 months of HFD. (FIG. 6D) Quantification of p-Smad2-positive area in the aortic valves of WT (n=5) and LDLR (n=10) mice after 6 months of HFD from immunohistochemical staining images represented in FIG. 6C.

FIGS. 7A-G. Generating the TGF-31platelet-KO-LDLR (Pf4Cre+Tgfb1f/f;Ldlr-/-Apob100/100) mice and their littermate TGF-β1flox-LDLR controls (Tgfb1f/f;Ldlr-/-Apob100/100). (FIG. 7A) Schematic diagram of the breeding protocol to generate TGF-β1platelet-KO-LDLR mice and their littermate controls (FIG. 7B). Punnet square of all heterozygous crossings (Pf4Cre+/-Tgfb1+/f;Ldlr+/-Apob100/wt X Pf4Cre+/-Tgfb1+/f;Ldlr+/-Apob100/wt) and the resulting genotypes. (FIG. 7C) Serum TGF-β1 levels in mice with no Pf4Cre and mice, which have Pf4Cre and are heterozygous or homozygous for Tgfb1f, at 6 months on HFD. (FIG. 7D) Aortic stenosis parameter—fractional valve opening, in WT, littermate TGF-β1flox-LDLR control, mixed genotype (Pf4Cre+Tgfb+/f;Ldlr-/-Apob100/wt, Pf4Cre+Tgfbf/f;Ldlr+/-Apob100/wt and Pf4Cre+Tgfbf/f, Ldlr-/-Apobwt/wt), and TGF-β1platelet-KO-LDLR mice at 6 months on HFD. (FIG. 7E) Plasma cholesterol levels in littermate controls-TGF-β1flox-LDLR, mixed genotype, and TGF-β1platelet-KO-LDLR mice at 6 months on HFD. (FIG. 7F) Representative images of p-Smad2 immunohistochemical staining in TGF-β1platelet-KO-LDLR and littermate TGF-β1flox-LDLR control mice at 6 months on HFD. (FIG. 7G) Whole mount staining of aortic valves for CD41, CD62P, p-Smad2 and DAPI in TGF-β1platelet-KO-LDLR and littermate TGF-β1flox-LDLR control mice. Co-localization analysis for CD41 and CD62P, and p-Smad2 and DAPI, in whole mount confocal single z-stack plane is shown in the table below.

FIGS. 8A-F. Aortic valvular endothelial cells transform into myofibroblasts to produce collagen. (FIG. 8A) Vimentin, (FIG. 8B) p-Smad2, (FIG. 8C) α-SMA and (FIG. 8D) Vimentin, α-SMA, and DAPI immunofluorescent stained aortic valves of LDLR mice after 6 months of HFD. (FIG. 8E) Immunofluorescent staining of collagen, PR2D3, TE7, and ER-TR7 in aortic valves from LDLR and WT mice after 6 months of HFD. (FIG. 8F) Graphic representation of an aortic stenosis model showing the role of shear, platelets, and TGF-β1 in stenosis progression.

FIGS. 10A-F. Graphic representation of echocardiography methodology and the representative images used to obtain aortic stenosis parameters. (FIGS. 10A-C) Modified aortic arch view. (FIG. 10D) Calculation of aortic valve peak velocity and WSS using the modified aortic arch view. (FIGS. 10E-F) Parasternal long axis view, and calculation of LVOT using this view.

FIGS. 11A-C. Graphic representation of echocardiography methodology and the representative images used to obtain heart function parameters. (FIGS. 11A-B) Short axis view. (FIG. 11C) Calculation of heart function parameters using m-mode of short axis view.

FIG. 12. Graphical representation showing the plane of sectioning necessary to get to the middle of the two aortic valve leaflets (where they are at their thickest) for histology.

FIG. 13. Figure showing quantification methodology for immuno-histochemically and histochemically stained aortic valves.

DETAILED DESCRIPTION OF ILLUSTRATIVE EMBODIMENTS

Figure 1G:
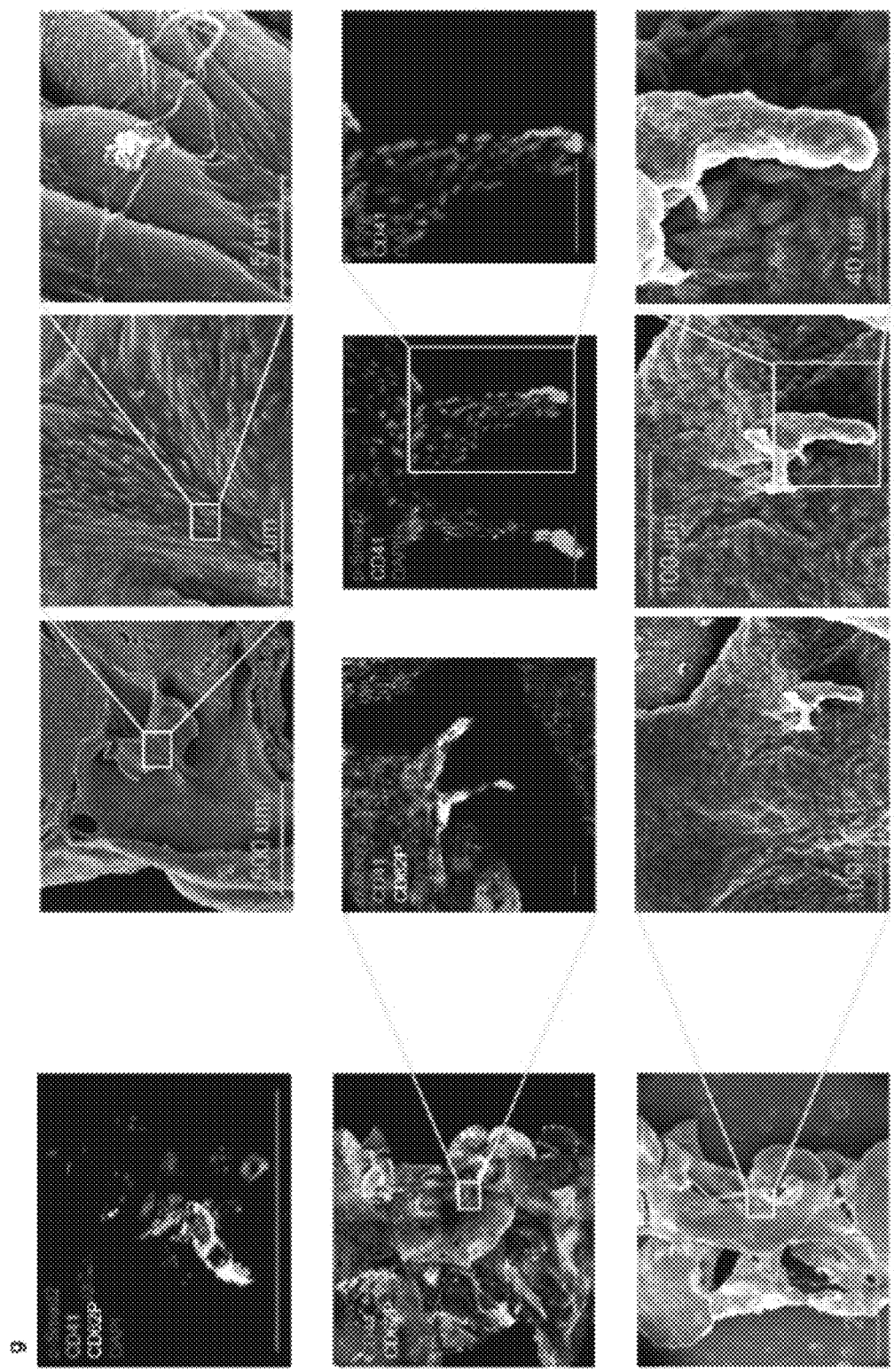

Heart disease is one of the leading causes of morbidity and mortality in the world. In the U.S. alone, estimates indicate that 3 million people are currently living with cardiomyopathy and another 400,000 are diagnosed on a yearly basis. Heart disease and its manifestations, including coronary artery disease, myocardial infarction, congestive heart failure and cardiac hypertrophy, clearly presents a major health risk in the United States today. The cost to diagnose, treat and support patients suffering from these diseases is well into the billions of dollars.

Aortic stenosis (AS) is a common heart condition that, if left untreated, can lead to heart failure and death. AS stages are diagnosed by the degree of aortic valve narrowing and increased wall shear stress WSS across the valve (Gould et al., 2013; Otto, 2006). The only treatment for AS is surgical valve replacement, therefore a therapeutic drug to mitigate AS is critically needed. The inventor has shown that AS progression is associated with increased plasma levels of TGF-β1 in mice (Wang et al., 2014). TGF-β1 stimulates fibrosis by inducing cells to produce collagen via canonical Smad signaling. TGF-β1 is abundant in platelets, which express 40-100-fold more TGF-β1 than any other cell type (Assoian et al., 1983), and secrete it as an inactive (latent) form, called large latent complex (LLC). The inventor previously demonstrated that shear force/shear stress can dramatically activate LLC (Ahamed et al., 2008).

The inventor established a robust mouse model of AS by feeding hyperlipidemic Ldlr(-/-) Apob(100/100) (LDLR) mice a high fat diet (HFD) from six-weeks of age. He found that LDLR mice lacking platelet-derived TGF-β1 (TGF-β1$^{platelet-KO}$-LDLR) were protected from developing AS compared to control mice on HFD. He also now provides evidence that platelet-derived TGF-β1 activates TGF-β signaling in valvular cells, triggering their transformation into collagen-producing myofibroblasts. The inventor treated these mice with N-acetylcysteine (NAC), which blocks shear-induced TGF-β1 activation in vitro (Ahamed et al., 2008). NAC significantly attenuated different stages of AS progression in LDLR mice but did not show any effect in TGF-β1$^{platelet-KO}$-LDLR mice, suggesting that NAC halts AS progression by blocking platelet-derived TGF-β1 activation. Thus, inhibiting platelet-derived TGF-β1 represents a potential non-invasive therapeutic intervention for aortic stenosis. Recent data by the inventor shows NAC treatment inhibits cardiac fibrosis in a high shear pressure overload ascending aortic contriction (AAC) model (data not shown).

Taken together these data support the idea that NAC can prevent organ fibrosis by selectively inhibiting shear-dependent TGF-β1 activation.

These and other aspects of the disclosure are described in detail below.

I. AORTIC STENOSIS

Aortic valve stenosis, also termed aortic stenosis or fibrocalcific aortic stenosis (AS, AVS, or AoS), is the narrowing of the exit of the left ventricle of the heart (where the aorta begins), such that problems result. It may occur at the aortic valve or above and below this level, and typically worsens over time. Symptoms often occur gradually, with a decreased ability to exercise often occurring first. If heart failure, loss of consciousness, or heart-related chest pain occurs due to AS, the outcomes are worse. Loss of consciousness typically occurs with standing or exercise. Signs of heart failure include shortness of breath, especially when lying down, at night, or with exercise, and swelling of the legs. Thickening of the valve without narrowing is known as aortic sclerosis.

Causes include being born with a bicuspid aortic valve and rheumatic fever, the former occurring in about one to two percent of the population, while the latter primarily occurs in developing nations. A normal valve, however, may also spontaneously harden over the decades. Risk factors are similar to those of coronary artery disease and include smoking, high blood pressure, high cholesterol, diabetes and male gender. The aortic valve usually has three leaflets and is located between the left ventricle of the heart and the aorta. AS severity can be divided into mild, moderate, severe, and very severe based on ultrasound assessments of the heart.

Aortic stenosis, once diagnosed, is typically followed using repeat ultrasounds. Once it has become severe, treatment primarily involves valve replacement surgery, with transcatheter aortic valve replacement (TAVR) being an option in some who are at high risk from surgery. Valves may either be mechanical or bioprosthetic, each having risks and benefits. Another less invasive procedure, balloon aortic valvuloplasty (BAV), may have a beneficial, but temporary (a few months) result. Complications such as heart failure may be treated as per normal in those with mild to moderate AS. In those with severe disease, a number of medications should be avoided, including ACE inhibitors, nitroglycerin, and some beta blockers. Nitroprusside or phenylephrine may be used in those with decompensated heart failure depending on their blood pressure.

Aortic stenosis is the most common valvular heart disease in the developed world, affecting approximately 2% of people over 65 years of age. Estimated rates are not known in most of the developing world as of 2014. In those who have symptoms, without repair, the 5-year mortality rate is about 50%, and at 10 years nearly 90%. Aortic stenosis was first described by French physician Lazare Rivière in 1663.

1. Symptoms and Complications

Symptoms related to aortic stenosis depend on the degree of stenosis. Most people with mild to moderate aortic stenosis are asymptomatic. Symptoms usually present in individuals with severe aortic stenosis, though they may also occur in mild to moderate aortic stenosis. The three main symptoms of aortic stenosis are loss of consciousness, anginal chest pain and shortness of breath with activity or other symptoms of heart failure such as shortness of breath while lying flat, episodes of shortness of breath at night, or swollen legs and feet. It may also be accompanied by the characteristic "Dresden china" appearance of pallor with a light flush.

Angina in setting of heart failure also increases the risk of death. In people with angina, the 5-year mortality rate is 50% if the aortic valve is not replaced. Angina in the setting of AS occurs due to left ventricular hypertrophy (LVH) caused by the constant production of increased pressure required to overcome the pressure gradient caused by the AS. While the muscular layer of the left ventricle thickens, the arteries that supply the muscle do not get significantly longer or bigger, so the muscle may not receive enough blood supply to meet its oxygen requirement. This ischemia may first be evident during exercise when the heart muscle requires increased blood supply to compensate for the increased workload. The individual may complain of anginal chest pain with exertion. At this stage, a cardiac stress test with imaging may be suggestive of ischemia.

Eventually, however, the heart muscle will require more blood supply at rest than can be supplied by the coronary artery branches. At this point, there may be signs of ventricular strain pattern (ST segment depression and T wave inversion) on the EKG, suggesting subendocardial ischemia. The subendocardium is the region most susceptible to ischemia because it is the most distant from the epicardial coronary arteries.

Syncope (fainting spells) from aortic valve stenosis is usually exertional and, in heart failure, increases the risk of death, e.g., the 3 year mortality rate is 50% if the aortic valve is not replaced. It is unclear why aortic stenosis causes syncope. One theory is that severe AS produces a nearly fixed cardiac output. When a person with aortic stenosis exercises, their peripheral vascular resistance decreases as the blood vessels of the skeletal muscles dilate to allow the muscles to receive more blood to allow them to do more work. This decrease in peripheral vascular resistance is normally compensated for by an increase in cardiac output, but since people with severe AS cannot increase their cardiac output, their blood pressure falls and the person will faint due to decreased blood perfusion to the brain.

A second theory as to why syncope may occur in AS is that during exercise, the high pressures generated in the hypertrophied left ventricle cause a vasodepressor response, which causes a secondary peripheral vasodilation that, in turn, causes decreased blood flow to the brain resulting in loss of consciousness. Indeed, in aortic stenosis, because of the fixed obstruction to blood flow out from the heart, it may be impossible for the heart to increase its output to offset peripheral vasodilation.

A third mechanism may sometimes be operative. Due to the hypertrophy of the left ventricle in aortic stenosis, including the consequent inability of the coronary arteries to adequately supply blood to the myocardium (see "Angina" below), abnormal heart rhythms may develop that can lead to syncope.

Finally, in calcific aortic stenosis at least, calcification in and around the aortic valve can progress and extend to involve the electrical conduction system of the heart, which may result in heart block, a potentially lethal condition for which syncope may be a symptom.

Congestive heart failure (CHF) carries a grave prognosis in people with AS. People with CHF attributable to AS have a 2-year mortality rate of 50% if the aortic valve is not replaced. CHF in the setting of AS is due to a combination of left ventricular hypertrophy with fibrosis, systolic dysfunction (a decrease in the ejection fraction) and diastolic dysfunction (elevated filling pressure of the LV).

In Heyde's syndrome, aortic stenosis is associated with gastrointestinal bleeding due to angiodysplasia of the colon. Recent research has shown that the stenosis causes a form of von Willebrand disease by breaking down its associated coagulation factor (factor VIII-associated antigen, also called von Willebrand factor) due to increased turbulence around the stenotic valve.

Notwithstanding the foregoing, the American Heart Association has changed its recommendations regarding antibiotic prophylaxis for endocarditis. Specifically, as of 2007, it is recommended that such prophylaxis should be limited only to those with prosthetic heart valves, those with previous episode(s) of endocarditis, and those with certain types of congenital heart disease.

Since the stenosed aortic valve may limit the hearts output, people with aortic stenosis are at risk of syncope and dangerously low blood pressure should they use any of a number of medications for cardiovascular diseases that often coexist with aortic stenosis. Examples include nitroglycerin, nitrates, ACE inhibitors, terazosin (Hytrin), and hydralazine, all substances that lead to peripheral vasodilation. Under normal circumstances, in the absence of aortic stenosis, the heart is able to increase its output and thereby offset the effect of the dilated blood vessels. In some cases of aortic stenosis, however, due to the obstruction of blood flow out of the heart caused by the stenosed aortic valve, cardiac output cannot be increased. Low blood pressure or syncope may ensue.

2. Causes and Pathophysiology

Aortic stenosis is most commonly caused by age-related progressive calcification (>50% of cases) with a mean age of 65 to 70 years. Another major cause of aortic stenosis is the calcification of a congenital bicuspid aortic valve (30-40% of cases) typically presenting earlier, in those aged 40+ to 50+.

Acute rheumatic fever post-inflammatory is the cause of less than 10% of cases. Rare causes of aortic stenosis include Fabry disease, systemic lupus erythematosus, Paget disease, high blood uric acid levels, and infection.

Density-dependent colour scanning electron micrograph of cardiovascular calcification, showing in orange calcium phosphate spherical particles (denser material) and, in green, the extracellular matrix (less dense material).

The human aortic valve normally consists of three cusps or leaflets and has an opening of 3.0-4.0 square centimeters. When the left ventricle contracts, it forces blood through the valve into the aorta and subsequently to the rest of the body. When the left ventricle expands again, the aortic valve closes and prevents the blood in the aorta from flowing backward (regurgitation) into the left ventricle. In aortic stenosis, the opening of the aortic valve becomes narrowed or constricted (stenotic) (i.e., due to calcification). Degenerative aortic stenosis, the most common variety, and bicuspid aortic stenosis both begin with damage to endothelial cells from increased mechanical stress. Inflammation is thought to be involved in the earlier stages of the pathogenesis of AS and its associated risk factors are known to promote the deposition of LDL cholesterol and a highly damaging substance known as Lipoprotein(a) into the aortic valve resulting in significant damage and stenosis over time.

As a consequence of this stenosis, the left ventricle must generate a higher pressure with each contraction to effectively move blood forward into the aorta. Initially, the LV generates this increased pressure by thickening its muscular walls (myocardial hypertrophy). The type of hypertrophy most commonly seen in AS is known as concentric hypertrophy, in which the walls of the LV are (approximately) equally thickened.

In the later stages, the left ventricle dilates, the wall thins, and the systolic function deteriorates (resulting in impaired ability to pump blood forward). Morris and Innasimuthu et al. showed that different coronary anatomy is associated with different valve diseases. Research is ongoing to see if different coronary anatomy might lead to turbulent flow at the level of valves leading to inflammation and degeneration.

3. Diagnosis

Aortic stenosis is most often diagnosed when it is asymptomatic and can sometimes be detected during routine examination of the heart and circulatory system. Good evidence exists to demonstrate that certain characteristics of the peripheral pulse can rule in the diagnosis. In particular, there may be a slow and/or sustained upstroke of the arterial pulse, and the pulse may be of low volume. This is sometimes referred to as pulsus parvus et tardus. There may also be a noticeable delay between the first heart sound (on auscultation) and the corresponding pulse in the carotid artery (so-called 'apical-carotid delay'). In a similar manner, there may be a delay between the appearance of each pulse in the brachial artery (in the arm) and the radial artery (in the wrist).

The first heart sound may be followed by a sharp ejection sound ("ejection click") best heard at the lower left sternal border and the apex, and thus appear to be "split". The ejection sound, caused by the impact of left ventricular outflow against the partially fused aortic valve leaflets, is more commonly associated with a mobile bicuspid aortic valve than an immobile calcified aortic valve. The intensity of this sound does not vary with respiration, which helps distinguish it from the ejection click produced by a stenotic pulmonary valve, which will diminish slightly in intensity during inspiration.

An easily heard systolic, crescendo-decrescendo (i.e., 'ejection') murmur is heard loudest at the upper right sternal border, at the 2nd right intercostal space, and radiates to the carotid arteries bilaterally. The murmur increases with squatting and decreases with standing and isometric muscular contraction such as the Valsalva maneuver, which helps distinguish it from hypertrophic obstructive cardiomyopathy (HOCM). The murmur is louder during expiration but is also easily heard during inspiration. The more severe the degree of the stenosis, the later the peak occurs in the crescendo-decrescendo of the murmur.

The second heart sound ($A_2$) tends to become decreased and softer as the aortic stenosis becomes more severe. This is a result of the increasing calcification of the valve preventing it from "snapping" shut and producing a sharp, loud sound. Due to increases in left ventricular pressure from the stenotic aortic valve, over time the ventricle may hypertrophy, resulting in a diastolic dysfunction. As a result, one may hear a fourth heart sound due to the stiff ventricle. With continued increases in ventricular pressure, dilatation of the ventricle will occur, and a third heart sound may be manifest.

Finally, aortic stenosis often co-exists with some degree of aortic insufficiency (aortic regurgitation). Hence, the physical exam in aortic stenosis may also reveal signs of the latter, for example, an early diastolic decrescendo murmur. Indeed, when both valve abnormalities are present, the expected findings of either may be modified or may not even be present. Rather, new signs that reflect the presence of simultaneous aortic stenosis and insufficiency, e.g., pulsus bisferiens, emerge.

According to a meta analysis, the most useful findings for ruling in aortic stenosis in the clinical setting were slow rate of rise of the carotid pulse (positive likelihood ratio ranged 2.8-130 across studies), mid to late peak intensity of the murmur (positive likelihood ratio, 8.0-101), and decreased intensity of the second heart sound (positive likelihood ratio, 3.1-50).

Other peripheral signs include sustained, heaving apex beat that is not displaced unless systolic dysfunction of the left ventricle has developed, a precordial thrill and narrowed pulse pressure Although aortic stenosis does not lead to any specific findings on the electrocardiogram (ECG), it still often leads to a number of electrocardiographic abnormalities. ECG manifestations of left ventricular hypertrophy (LVH) are common in aortic stenosis and arise as a result of the stenosis having placed a chronically high pressure load on the left ventricle (with LVH being the expected response to chronic pressure loads on the left ventricle no matter what the cause).

As noted above, the calcification process that occurs in aortic stenosis can progress to extend beyond the aortic valve and into the electrical conduction system of the heart. Evidence of this phenomenon may rarely include ECG patterns characteristic of certain types of heart block such as Left bundle branch block.

Cardiac chamber catheterization provides a definitive diagnosis, indicating severe stenosis in valve area of <1.0 $cm^2$ (normally about 3 $cm^2$), by directly measuring the pressure on both sides of the aortic valve. The pressure gradient may be used as a decision point for treatment and is useful in symptomatic patients before surgery. The standard for diagnosis of aortic stenosis is noninvasive testing with echocardiography. Cardiac catheterization is reserved for cases in which there is discrepancy between the clinical picture and non-invasive testing, due to risks inherent to crossing the aortic valve such as stroke.

Echocardiogram (heart ultrasound) is the best non-invasive tool/test to evaluate aortic valve anatomy and function. The aortic valve area can be calculated non-invasively using echocardiographic flow velocities. Using the velocity of the blood through the valve, the pressure gradient across the valve can be calculated by the continuity equation or using the modified Bernoulli's equation:

$$\text{Gradient}=4(\text{velocity})^2 \text{ mmHg}$$

A normal aortic valve has a gradient of only a few mmHg. A decreased valvular area causes increased pressure gradient, and these parameters are used to classify and grade the aortic stenosis as mild, moderate or severe. The pressure gradient can be abnormally low in the presence of mitral stenosis, heart failure, co-existent aortic regurgitation and also ischaemic heart disease (disease related to decreased blood supply and oxygen causing ischemia).

Echocardiograms may also show left ventricular hypertrophy, thickened and immobile aortic valve and dilated aortic root, although it may appear deceptively normal in acute cases.

A chest X-ray can also assist in the diagnosis and provide clues as to the severity of the disease, showing the degree of calcification of the valve, and in a chronic condition, an enlarged left ventricle and atrium.

4. Management

Treatment is generally not necessary in asymptomatic patients. In moderate cases, echocardiography is performed every 1-2 years to monitor progression, possibly complemented with a cardiac stress test. In severe cases, echocardiography is performed every 3-6 months. In both moderate and mild cases, the person should immediately make a revisit or be admitted for inpatient care if any new related symptoms appear. There are no therapeutic options currently available to treat people with aortic valve stenosis, however, studies have indicated that the disease occurs as a result of active cellular processes, suggesting that targeting these processes may lead to viable therapeutic approaches.

The effect of statins on the progression of AS is unclear. The latest trials do not show any benefit in slowing AS progression, but did demonstrate a decrease in ischemic cardiovascular events.

In general, medical therapy has relatively poor efficacy in treating aortic stenosis. However, it may be useful to manage commonly coexisting conditions that correlate with aortic stenosis. Any angina is generally treated with beta-blockers and/or calcium blockers. Nitrates are contraindicated due to their potential to cause profound hypotension in aortic stenosis. Any hypertension is treated aggressively, but caution must be taken in administering beta-blockers. Any heart failure is generally treated with digoxin and diuretics, and, if not contraindicated, cautious administration of ACE inhibitors.

While observational studies demonstrated an association between lowered cholesterol with statins and decreased progression, a randomized clinical trial published in 2005 failed to find any effect on calcific aortic stenosis. A 2007 study did demonstrate a slowing of aortic stenosis with the statin rosuvastatin.

Aortic valve repair or aortic valve reconstruction describes the reconstruction of both form and function of the native and dysfunctioning aortic valve. Most frequently it is applied for the treatment of aortic regurgitation. It can also become necessary for the treatment of an aortic aneurysm, and less frequently for congenital aortic stenosis.

In adults, symptomatic severe aortic stenosis usually requires aortic valve replacement (AVR). While AVR has been the standard of care for aortic stenosis for several decades, currently these approach include open heart surgery, minimally invasive cardiac surgery (MICS) and minimally invasive catheter-based (percutaneous) aortic valve replacement. However, surgical aortic valve replacement is well studied and generally has a good and well-established longer term prognosis.

A diseased aortic valve is most commonly replaced using a surgical procedure with either a mechanical or a tissue valve. The procedure is done either in an open-heart surgical procedure or, in a smaller but growing number of cases, a minimally invasive cardiac surgery (MICS) procedure.

Globally more than 250,000 people have received transcatheter aortic valve replacement (TAVR). For people who are not candidates for surgical valve replacement and most patients who are older than 75, TAVR may be a suitable alternative. However, TAVR may generate disturbed flow due to unrepairable leakage, which can have a deteriorating effect due to activation of platelet TGF-β1. Further studies are needed to evaluate such effects.

For infants and children, balloon valvuloplasty, wherein a balloon is inflated to stretch the valve and allow greater flow, may also be effective. In adults, however, it is generally ineffective, as the valve tends to return to a stenosed state. The surgeon makes a small incision at the top of the person's leg and proceeds to insert the balloon into the artery. The balloon is then advanced up to the valve and inflated to stretch the valve open.

Acute decompensated heart failure due to AS may be temporarily managed by an intra-aortic balloon pump pending surgery. In those with high blood pressure, nitroprusside may be carefully used. Phenylephrine may be used in those with very low blood pressure.

II. N-ACETYLCYSTEINE

Acetylcysteine, also known as N-acetylcysteine (NAC), is a medication used for the treatment of paracetamol (acetaminophen) overdose and to loosen thick mucus in individuals with cystic fibrosis or chronic obstructive pulmonary disease. It can be taken intravenously, by mouth, or inhaled as a mist. Some people use it as a dietary supplement.

A. Side Effects

Common side effects include nausea and vomiting when taken by mouth. The skin may occasionally become red and itchy with either form. A non-immune type of anaphylaxis may also occur. It appears to be safe in pregnancy. It works by increasing glutathione levels and binding with the toxic breakdown products of paracetamol.

Acetylcysteine was initially patented in 1960 and licensed for use in 1968. It is on the World Health Organization's List of Essential Medicines, the most effective and safe medicines needed in a health system. It is available as a generic medication and is not very expensive.

The most commonly reported adverse effects for IV formulations of acetylcysteine are rash, urticaria, and itchiness. Up to 18% of patients have been reported to experience anaphylaxis reaction, which are defined as rash, hypotension, wheezing, and/or shortness of breath. Lower rates of anaphylactoid reactions have been reported with slower rates of infusion.

Adverse effects for inhalational formulations of acetylcysteine include nausea, vomiting, stomatitis, fever, rhinorrhea, drowsiness, clamminess, chest tightness, and bronchoconstriction. Though infrequent, bronchospasm has been reported to occur unpredictably in some patients.

Adverse effects for oral formulations of acetylcysteine have been reported to include nausea, vomiting, rash, and fever.

Antioxidants are widely used to protect cells from damage induced by reactive oxygen species (ROS). The concept that antioxidants can help fight cancer is deeply rooted in the general population, promoted by the food supplement industry. However, clinical trials have reported inconsistent results. High levels of ROS or prolonged stress upregulates p53 and provokes a pro-oxidant response to further increase ROS, which subsequently elicits the p53-dependent apoptotic processes to eliminate damaged cells. Thus, antioxidants can accelerate tumor growth by disrupting the ROS-p53 axis apoptosis and autophagy processes. Because somatic mutations in p53 occur late in tumor progression, antioxidants may accelerate the growth of early tumors or precancerous lesions in high-risk populations such as smokers and patients with chronic obstructive pulmonary disease who receive NAC to relieve mucus production. It is not clear what dose(s) induce these effects. Additionally, it is important to reiterate that NAC does not cause cancer, it counteracts ROS accumulation caused by p53 and down-regulates p53, which in turn prevents p53-induced apoptosis and promotes autophagy. In all cells, it is a dose-dependent response, and the ability to manipulate cellular apoptosis and autophagy has many therapeutic benefits.

Large doses in a mouse model showed that acetylcysteine could potentially cause damage to the heart and lungs. They found that acetylcysteine was metabolized to S-nitroso-N-acetylcysteine (SNOAC), which increased blood pressure in the lungs and right ventricle of the heart (pulmonary artery hypertension) in mice treated with acetylcysteine. The effect was similar to that observed following a 3-week exposure to an oxygen-deprived environment (chronic hypoxia). The authors also found that SNOAC induced a hypoxia-like response in the expression of several important genes both in vitro and in vivo.

The implications of these findings for long-term treatment with acetylcysteine have not yet been investigated. The dose used by Palmer and colleagues was dramatically higher than that used in humans, the equivalent of about 20 grams per day. Nonetheless, positive effects on age-diminished control of respiration (the hypoxic ventilatory response) have been observed previously in human subjects at more moderate doses.

Although N-acetylcysteine prevented liver damage when taken before alcohol, when taken 4 hours after alcohol, it actually made liver damage worse in a dose-dependent fashion.

B. Pharmacology and Pharmacodynamics

Acetylcysteine serves as a prodrug to L-cysteine. L-cysteine is a precursor to the biologic antioxidant glutathione. Hence administration of acetylcysteine replenishes glutathione stores.

Glutathione, along with oxidized glutathione (GSSG) and S-nitrosoglutathione (GSNO), have been found to bind to the glutamate recognition site of the NMDA and AMPA receptors (via their γ-glutamyl moieties), and may be endogenous neuromodulators. At millimolar concentrations, they may also modulate the redox state of the NMDA receptor complex. In addition, glutathione has been found to bind to and activate ionotropic receptors that are different from any other excitatory amino acid receptor, and which may constitute glutathione receptors, potentially making it a neurotransmitter. As such, since N-acetylcysteine is a prodrug of glutathione, it may modulate all of the aforementioned receptors as well.

Glutathione also modulates the NMDA receptor by acting at the redox site. L-cysteine also serves as a precursor to cystine which in turn serves as a substrate for the cystine-glutamate antiporter on astrocytes hence increasing glutamate release into the extracellular space. This glutamate in turn acts on $mGluR_{2/3}$ receptors, and at higher doses of acetylcysteine, $mGluR_5$. Acetylcysteine also possesses some anti-inflammatory effects possibly via inhibiting NF-κB and modulating cytokine synthesis.

NAC is extensively liver metabolized; CYP450 minimal. Urine excretion 22-30% with a half-life of 5.6 hours in adults and 11 hours in neonates.

C. Chemistry

Acetylcysteine is the N-acetyl derivative of the amino acid L-cysteine, and is a precursor in the formation of the antioxidant glutathione in the body. The thiol (sulfhydryl) group confers antioxidant effects and is able to reduce free radicals.

N-acetyl-L-cysteine is soluble in water and alcohol, and practically insoluble in chloroform and ether.

It is a white to white with light yellow cast powder, and has a pKa of 9.5 at 30° C.

D. Dosage Forms

Acetylcysteine is available in the following different dosage forms for different indications:

Solution for inhalation (Assist, Mucomyst, Mucosil)—inhaled for mucolytic therapy or ingested for nephroprotective effect (kidney protection)

Intravenous injection (Assist, Parvolex, Acetadote)—treatment of paracetamol/acetaminophen overdose Oral solution—various indications.

Effervescent tablets

Ocular solution—for mucolytic therapy

Tablets—sometimes in a sustained release formula sold as a nutritional supplement Capsules The IV injection and inhalation preparations are, in general, prescription only, whereas the oral solution and the effervescent tablets are available over the counter in many countries. Acetylcysteine is available as a health supplement in the United States, typically in capsule form.

III. METHODS OF TREATING FIBROSIS AND AORTIC STENOSIS

As discussed above, the present disclosure provides for new therapies for organ fibrosis and aortic stenosis. In one embodiment of the present disclosure, methods for the treatment of subjects provides for one or more of the following outcomes as compared to an untreated patient. For example, in the context of cardiovascular fibrosis/aortic stenosis, increased exercise capacity, increased blood ejection volume, decreased left ventricular end diastolic pressure, decreased pulmonary capillary wedge pressure, increased cardiac output, improved cardiac index, decreased pulmonary artery pressures, decreased left ventricular end systolic and diastolic dimensions, and decreased left ventricular wall stress, decreased wall tension and decreased wall thickness-same for the right ventricle are contemplated. In addition, the treatment may prevent progression to cardiac hypertrophy, fibrosis, and ultimately heart failure.

Treatment regimens will vary depending on the clinical situation. However, in general, the treatment would begin at a time following a formal diagnosis of aortic stenosis, or upon clinical signs highly suggestive of aortic stenosis. The patient may or may not be undergoing one or more other therapies for prevention or treatment of another cardiance condition. The therapy may continue for as long as is needed, including 7, 14, 21 and 28 days, or 1, 2, 3, or 6 months, a year, or indefinitely.

A. Drug Formulations and Routes for Administration to Patients

Where clinical applications are contemplated, pharmaceutical compositions will be prepared in a form appropriate for the intended application. Generally, this will entail preparing compositions that are essentially free of pyrogens, as well as other impurities that could be harmful to humans or animals.

One will generally desire to employ appropriate salts and buffers to render drugs stable and allow for uptake by target cells. Aqueous compositions of the present disclosure comprise an effective amount of the drug dissolved or dispersed in a pharmaceutically acceptable carrier or aqueous medium. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present disclosure, its use in therapeutic compositions is contemplated. Supplementary active ingredients also can be incorporated into the compositions, provided they do not inactivate the drugs of the compositions.

The active compositions of the present disclosure may include classic pharmaceutical preparations. Administration of these compositions according to the present disclosure may be via any common route so long as the target tissue is available via that route. This includes oral, nasal, or buccal. Alternatively, administration may be by intradermal, subcutaneous, intramuscular, intraperitoneal or intravenous injection, or by direct injection into cardiac tissue. Such compositions would normally be administered as pharmaceutically acceptable compositions, as described supra.

The active compounds may also be administered parenterally or intraperitoneally. By way of illustration, solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agent, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the active compounds in an appropriate amount into a solvent along with any other ingredients (for example as enumerated above) as desired, followed by filtered sterilization. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof.

The compositions of the present disclosure generally may be formulated in a neutral or salt form. Pharmaceutically-acceptable salts include, for example, acid addition salts (formed with the free amino groups of the protein) derived from inorganic acids (e.g., hydrochloric or phosphoric acids, or from organic acids (e.g., acetic, oxalic, tartaric, mandelic, and the like. Salts formed with the free carboxyl groups of the protein can also be derived from inorganic bases (e.g., sodium, potassium, ammonium, calcium, or ferric hydroxides) or from organic bases (e.g., isopropylamine, trimethylamine, histidine, procaine and the like.

Upon formulation, solutions are preferably administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

B. Combined Therapies

In another embodiment, it is envisioned that NAC may be used in combination with other therapeutic modalities, such as those discussed above. Combinations may be achieved by administering to patients a single composition or pharmacological formulation that includes both agents, or by administering to patients two distinct compositions or formulations, at the same time. Alternatively, the one therapy may precede or follow administration of the other agent or therapy by intervals ranging from minutes to weeks. In embodiments where the agents/therapies are administered separately, one would generally ensure that a significant period of time did not expire between the time of each delivery, such that the agents/therapies would still be able to exert an advantageously combined effect on the subject. In such instances, it is contemplated that one would typically contact the cell with both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of the agents/therapies will be desired. In this regard, various combinations may be employed. By way of illustration, where NAC is "A" and the other agent or therapy is "B," the following permutations based on 3 and 4 total administrations are exemplary:

| | | | | | | |
|---|---|---|---|---|---|---|
| A/B/A | B/A/B | B/B/A | A/A/B | B/A/A | A/B/B | B/B/B/A | B/B/A/B |
| A/A/B/B | A/B/A/B | A/B/B/A | B/B/A/A | B/A/B/A | B/A/A/B | B/B/B/A | |
| A/A/A/B | B/A/A/A | A/B/A/A | A/A/B/A | A/B/B/B | B/A/B/B | B/B/A/B | |

Other combinations are likewise contemplated.

Angina associated with aortic stenosis is generally treated with beta-blockers and/or calcium blockers. Nitrates are contraindicated due to their potential to cause profound hypotension in aortic stenosis. Any hypertension is treated aggressively, but caution must be taken in administering beta-blockers. Any heart failure is generally treated with digoxin and diuretics, and, if not contraindicated, cautious administration of ACE inhibitors. Statins, though controversial, may also be used.

Aortic valve repair or aortic valve reconstruction describes the reconstruction of both form and function of the native and dysfunctioning aortic valve. Most frequently it is applied for the treatment of aortic regurgitation. It can also become necessary for the treatment of an aortic aneurysm, less frequently for congenital aortic stenosis.

In adults, symptomatic severe aortic stenosis usually requires aortic valve replacement (AVR). While AVR has been the standard of care for aortic stenosis for several decades, currently aortic valve replacement approaches include open heart surgery, minimally invasive cardiac surgery (MICS) and minimally invasive catheter-based (percutaneous) aortic valve replacement.

A diseased aortic valve is most commonly replaced using a surgical procedure with either a mechanical or a tissue valve. The procedure is done either in an open-heart surgical procedure or, in a smaller but growing number of cases, a minimally invasive cardiac surgery (MICS) procedure.

Globally more than 250,000 people have received transcatheter aortic valve replacement (TAVR). For people who are not candidates for surgical valve replacement and most patients who are older than 75, TAVR may be a suitable alternative.

For infants and children, balloon valvuloplasty, where a balloon is inflated to stretch the valve and allow greater flow, may also be effective. In adults, however, it is generally ineffective, as the valve tends to return to a stenosed state. The surgeon will make a small incision at the top of the person's leg and proceed to insert the balloon into the artery. The balloon is then advanced up to the valve and is inflated to stretch the valve open.

Acute decompensated heart failure due to AS may be temporarily managed by an intra-aortic balloon pump while pending surgery. In those with high blood pressure nitroprusside may be carefully used. Phenylephrine may be used in those with very low blood pressure.

IV. EXAMPLES

The following examples are included to further illustrate various aspects of the disclosure. It should be appreciated by those of skill in the art that the techniques disclosed in the examples which follow represent techniques and/or compositions discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Methods

Figure 7A:
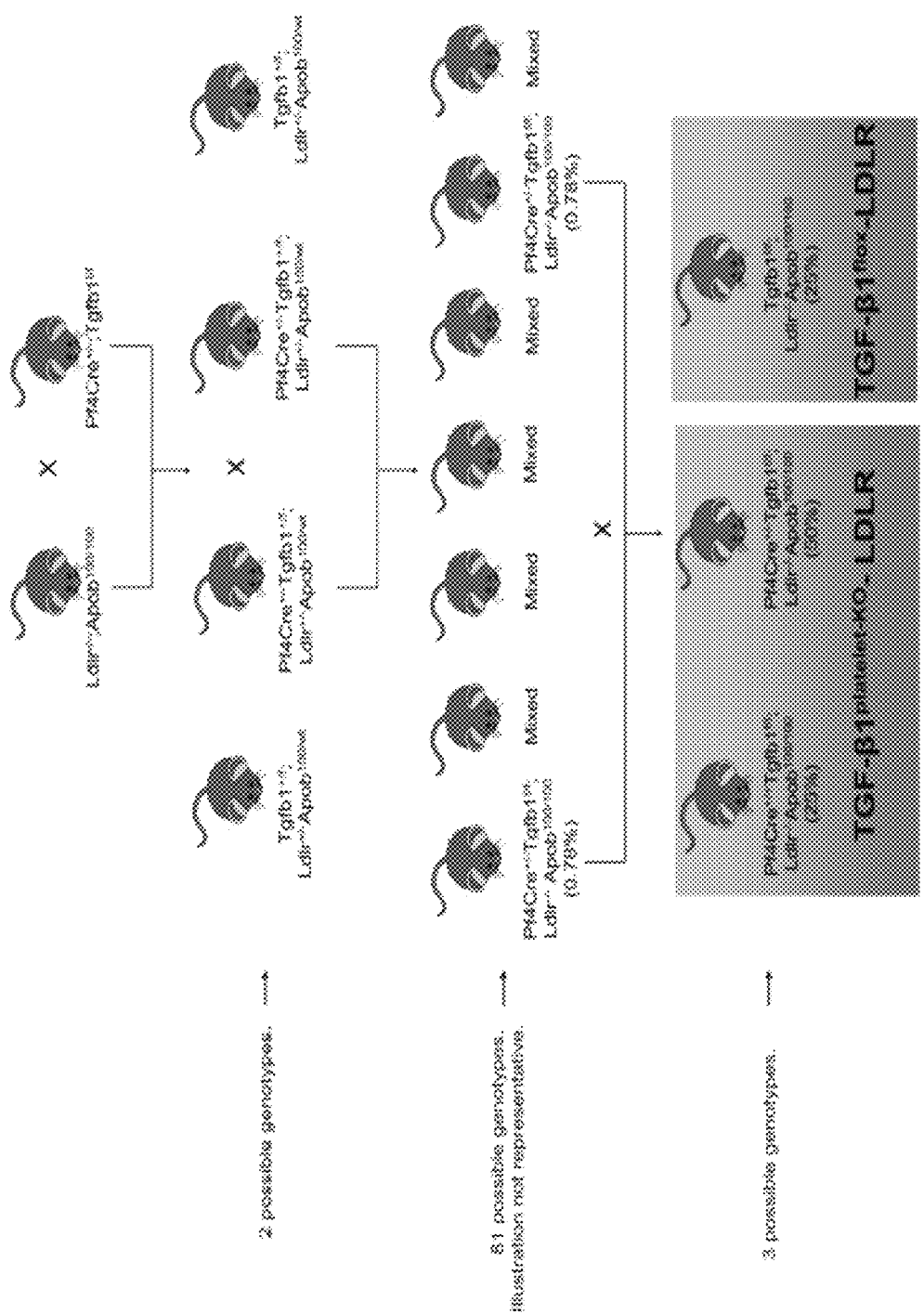

Mice. Hypercholesterolemic mice deficient for low-density lipoprotein receptors (Ldlr−/−), which only express ApoB-100 (Ldlr−/−Apob100/100, LDLR), were obtained from Jackson Laboratories (B6; 129SLdlrtm1HerApobtm2Sgy/J, stock no. 003000). WT C57bl/6 mice were also obtained from the Jackson Laboratory (stock no. 000664) and served as controls. TGF-$\beta1^{platelet-KO}$-LDLR mice (Pf4Cre+Tgfb1f/f;Ldlr−/−Apob100/100;) and TGF-$\beta1^{flox}$-LDLR littermate controls (Tgfb1f/f;Ldlr−/−Apob100/100) were generated by crossing LDLR mice with Pf4Cre+;Tgfb1f/f mice, as shown in FIGS. 7A-B and Supplemental Table 5. Genotyping and sequencing of megakaryocyte genomic DNA shows that Tgfb1 is inverted in Pf4Cre; Tgfb1$^{ff}$ animals, and depletion of TGF-$\beta1$ in platelets was confirmed by ELISA and immunoblotting with TGF-$\beta1$-specific antibodies. The inventor crossed Tie2Cre mice (stock no. 008863, Jackson Laboratories) with tdTomato lox-stop-lox mice (stock no. 007909, Jackson Laboratories) to generate Tie2Cre;tdTomato mice that express tdTomato only under Cre activity. All mice were housed in a controlled environment (23±2° C.; 12 hours light/dark cycles) and fed either a chow diet (CD) (Pico-Lab® Rodent Diet 20, 5053) or a customized high fat diet (HFD) (Harlan Teklad, TD.9612102. containing 21% milk fat (MF), 1.25% Cholesterol) in powdered form in a glass jar with perforated metal strainer (DYETS, Braintree Scientific Inc.). The Oklahoma Medical Research Foundation's Institutional Animal Care and Usage Committee approved all procedures.

Experimental Design. A total of 118 LDLR (58 Males, 60 Females) and 20 WT mice (10 Males, 10 Females) were used for this study. Half of the mice (6 weeks old) were switched to HFD and maintained for up to 9 months. Progression and severity (mild/moderate/severe) of AS were monitored at 0, 3, 6 and 9 months by echocardiography using non-invasive ultrasound imaging techniques. Five mice per cage (total of 25 males, 15 females) were treated with 2% N-acetylcysteine (NAC) (Acros Organics, 160280010) in drinking water. NAC was prepared in reverse osmosis water and its pH was adjusted to 7.4 with NaOH. Water was replaced with a fresh solution every week. NAC treatment was started and stopped at indicated time points as shown in FIG. 4B. The dose of NAC selected and activity and stability after dissolving in water for up to 15 days were validated by testing its effect on blocking shear-dependent TGF-$\beta1$ activation.

Preparation of mouse plasma. Mouse platelets and plasma were prepared from blood drawn by the inventor's previously described novel method that minimizes in vitro platelet activation (Meyer et al., 2012). Briefly, blood was drawn by retro-bulbar (RB) puncture in anesthetized mice and placed in a polypropylene tube containing 0.1 volume of 3.8% sodium citrate, pH 7.4. Immediately after blood drawing, plasma was prepared by centrifuging samples (12,000 g for 5 minutes at room temperature). Prostaglandin E1 (PGE1; 1 µM final concentration; Cayman Chemicals) was added to the blood collection tubes to prevent the release of platelet granule contents during blood drawing or plasma preparation.

TGF-$\beta1$ and Cholesterol measurement in plasma. Total TGF-$\beta1$ in platelets and plasma was measured with a 2-antibody ELISA assay specific for the activated form of TGF-$\beta1$ (DY240, R&D Systems) after converting latent TGF-$\beta1$ to active TGF-$\beta1$ by acidification (20-minute incubation at RT with 0.5 volume of 1 N HCl for plasma and 0.2 volume of 1 N HCl for platelet lysates and releasates, followed by neutralization by adding the same volume of 1.2 N NaOH in 0.5 M HEPES). Plasma cholesterol levels were measured using an enzymatic colorimetric assay (439-17501, Wako Diagnostics).

Echocardiography. Mice were anesthetized with Isoflurane (3-5% inhalation) in an induction chamber. Mice that appeared to be sick due to severe stenosis or that were underweight were anesthetized using a lower isoflurane level to prevent adverse or lethal effects from the anesthetic. Once visibly anesthetized, isoflurane was reduced to 0.5%-2% and the mouse was moved from the chamber to a nose-cone on a heated platform set at 40° C. to maintain body temperature (35±2° C.). Heavier mice were maintained at higher isoflurane levels as they appeared less sensitive to its anesthetic effects. All four limbs were taped to physiological electrodes and a rectal temperature probe was inserted. Electrode gel was used to enhance the physiologic readings. To ensure accuracy of all echo measurements, physiological parameters were monitored and recordings were only taken if the heart rate was 430-550 beats per minute, respiration was 20-100 breaths per minute, and body temperature was close to 37° C. (35±2° C.). Consistent heart rate is imperative for accurate heart function evaluation, and body temperature significantly affects heart rate (Gao et al., 2011).

Measurement of AS parameters using a modified view of ultrasound imaging. Echocardiography is the gold standard non-invasive method to measure AS in humans. However, the mouse heart rate is 10-times faster (500 to 600 beats per minute), making the acquisition of high-resolution images of the very thin non-diseased valves challenging. Thus, using B mode imaging with a Vevo 2100® transducer (VisualSonics, Toronto, Canada), we established an angle that resulted in very clear images of aortic valve leaflets, LVOT and peak blood flow velocity across the valve. LVOT was measured from the long-axis view and was used to calculate AV pressure and normalize the cusp separation (Lindman et al., 2016; Meyer et al., 2012). This view was obtained by tilting the lower left corner of the platform downward by about 30° and angling the transducer up such that it interfaced with the chest cavity by about 45°. The transducer was also rotated to 45° so the ends of the transducer ran parallel across the long axis of the heart from the front left limb to the back right foot (FIG. 10E). Modification of these placements and angles may be necessary to obtain the clearest image. A good PSLA view is defined as having clearly defined left ventricle walls and a continuous left ventricle from the aortic root to the apex of the heart. Moreover, it should lie completely horizontal in the visual plane and the right ventricle should be clearly seen on top of the left ventricle. The LVOT is the measured diameter of the location where the left ventricle meets the aorta, as illustrated in FIG. 10F.

For clear images of aortic valve cusps, an aortic arch view was obtained following a modified method as described by Pistner et al. (2010). This was achieved by angling the right side of the platform as downward as possible. The transducer was oriented so that it interfaced with left side of the mouse's body at approximately 45° and was rotated so that it ran parallel with the length of the mouse's body. Moving the transducer medially across the chest brings the valve into view to visualize both leaflets rapidly opening and closing (FIGS. 10A-B). If there was visual interference by the lung, the transducer was oriented at a shallower angle. Slight rotation of the transducer may be necessary to bring both aortic valve leaflets into view. After visualization of the aortic valve, high quality videos and images were captured using an ECG-Gated Kilohertz Visualization mode (EKV) in which the two leaflets can clearly be seen opening and closing (data not shown). The distance between the two cusps when the valve is fully open was measured (defined as Cusp Separation) and normalized over the LVOT, which is important in that it takes varying aortic sizes into account. This measure was defined as fractional valve opening. Thickness and area of the leaflets were also measured using ultrasound images and later confirmed histologically. Using a combination of color and power Doppler, blood flow velocity across the valves was measured. In this mode, red color defines blood flowing from the LV to the aorta and blue color blood flowing back from the aorta to the LV. The area in the middle where the color changes from red to blue is known as "aliasing", indicating which blood flow rate is highest. Aortic valve (AV) peak velocity (jet) is defined as the speed at which the blood flows across the AV at systole and is measured by placing a Pulse-Wave Doppler probe where the flow aliases and angling the probe so that it runs parallel with the flow (FIGS. 10C-D). The peak AV velocity and area of the curve of the Doppler waveform, known as the LVOT velocity time integral (VTI), was measured and used to calculate wall shear stress (WSS) and AV peak pressure (FIGS. 10A-F) (Meyer et al., 2012). AVA is the gold standard to determine AS severity in humans and it is measured directly using Planimetry and indirectly via Continuity Equation. We compared our AS parameters (fractional valve opening, peak velocity and calculated WSS) with AVA (calculated using the continuity equation and planimetry) in LDLR mice and found a strong correlation (data not shown). Our echo method directly measures both the area and velocity and is relatively easy to perform even in mice with 10 times faster heartbeats.

Systolic Cardiac Function. Left ventricle mass, volumes, and systolic heart functions were assessed using M-Mode images obtained from a Short Axis (SAX) view of the heart (FIGS. 11A-B). This view is well characterized and easily obtained by simply rotating the transducer 90° from the PSLA view so that the ventricle is cut across the short axis of the heart. Systolic heart function was measured by tracing the anterior and posterior walls of the left ventricle in an M-Mode view (FIG. 11C).

Histology and immunofluorescent staining of aortic valve sections. Mice receiving HFD were euthanized at 6 months and perfused with PBS. Hearts with their attached ascending aorta were excised, fixed in 4% paraformaldehyde for 24 hours and processed for routine paraffin embedding. Tissues were cut in 5 µm thick sections in the middle of the heart to get maximum valve thickness (FIG. 12) and stained with picrosirius red for collagen. For immunofluorescent staining, tissue sections were deparaffinized and rehydrated by immersing in xylene and a series of graded alcohols, followed by heat (97° C.)-induced epitope retrieval using Tris-EDTA buffer, pH 9.0 for 30 minutes. Slides were incubated for 1 hour at RT with blocking buffer (1% BSA+0.3M glycine in Tris-NaCl-Tween buffer) and then incubated overnight at 4° C. with primary antibodies at final concentrations of 0.5 µg/ml. After washing in wash buffer (Tris-NaCl-Tween) and incubation with a fluorescent secondary antibody at RT for 2 hours, slides were washed with wash buffer three times and mounted with a fluorescence mounting medium containing diamidino-2-phenylindole (DAPI) to stain nuclei.

Images were photographed using Ziess 710 Confocal or Nikon eclipse 80i fluorescence microscope. Positively-stained areas and total valve areas in immunohistochemical and histological images were quantified as shown in FIG. 13. Primary antibodies used were anti-phospho-Smad2 (Ser465/467) (AB3849, Millipore), anti-vimentin (ab92547, Abcam), anti-α-SMA (904601, Biolegend), Isolectin B4 (121411, Life Technologies), anti-CD41 (14-0411, eBioscience), anti-CD62P (148301, Biolegend), and anti-collagen (SAB1402151, Sigma). Species-matched secondary antibodies conjugated to Alexa 488, Alexa 594, or Alexa 647 were used. Histology images were analyzed and quantified using ImageJ (NIH).

Figure 14:
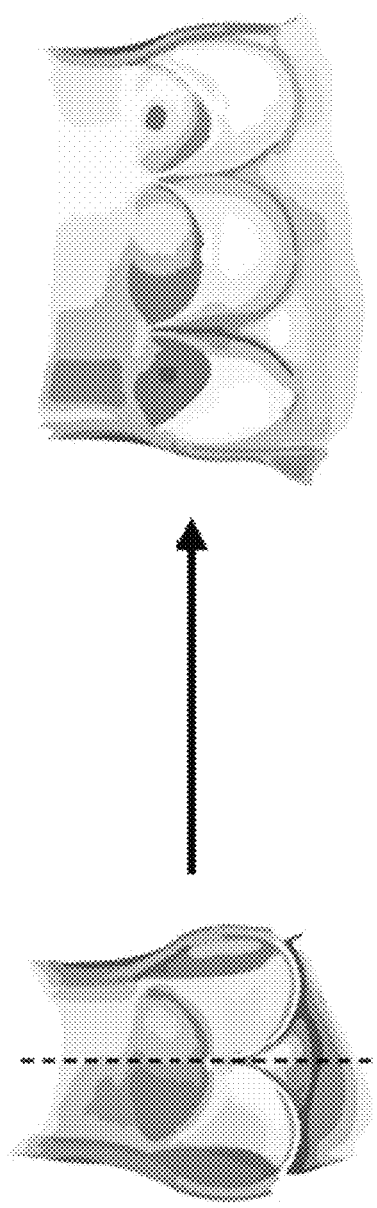
FIG. 14. Graphical representation of aortic valve micro-dissection for whole mount immunohistochemical staining and scanning electron microscopy.

Whole mount staining and confocal imaging. Whole aortic valve tissue, including some heart tissue, was harvested from HFD mice at 6 months and fixed overnight in 4% paraformaldehyde. Aortic root along with the aortic bulb was bisected, cut open and pinned on a dissecting petri dish under high-power surgical microscope to open the aortic valve leaflets flat (FIG. 14). Tissues were washed with PBS 3 times at 10 minutes per wash after fixation and permeabilized with PBS+0.3% triton X100 at 4° C. overnight on a shaker. Tissues were then blocked with PBS+0.3% triton+ 3% BSA at 4° C. overnight on a shaker. The tissues were incubated with primary antibodies (same as those listed in the above section) overnight on a shaker and at room temperature for 1 hour on a shaker the next day followed by washing with PBS+0.3% triton 3 times at 30 minutes each time at 4° C. on a shaker. Tissues were incubated in species-matched secondary antibodies (same as those noted in the above section) at room temperature for 2 hours or 4° C. overnight on a shaker in the dark followed by washing with PBS+0.1% triton 3 times, 30 minutes each time, at 4° C. on a shaker. The samples were mounted on glass slides using DAPI mounting medium (P36971, Life Technologies) and Coverwell Imaging Chambers (70327-10, EMS). Aortic valves were imaged using Ziess 710 Confocal microscope to obtain z-stacks and tiled pictures for co-localization analysis.

Scanning electron microscopy (SEM). Whole aortic valve tissues were harvested as shown in FIG. 14 from HFD mice at 6 months and fixed overnight in 4% paraformaldehyde. They were then fixed in 2% glutaraldehyde in 0.2 M cacodylate buffer for 2 hours at room temperature, rinsed three times for 15 minutes each in 0.1M cacodylate buffer, and fixed in 1% Osmium Tetroxide in 0.2M cacodylate buffer for 2 hours at room temperature. After rinsing three times, 15 minutes each, in 0.1M cacodylate buffer, the sections were serially dehydrated in 50, 70, 90, 95 and (3×) 100% ethanol, 15 minutes each. The sections were then placed in Hexamethyldisilazane 2× for 10 minutes and allowed to dry overnight in the chemical hood. Dried sections were then mounted on stubs with double-surfaced sticky tape and coated with Au—Pd before SEM imaging.

Ascending Aortic Constriction. Ascending aortic constriction was induced by controlled constriction of the ascending aorta as described previously 26. Briefly, mice were anesthetized with 1.5% isoflurane and the ascending aorta was surgically exposed by a mid-thorax incision. A 2 7-0 suture was placed around both the aorta and an adjacent 27-gauge (0.41 mm OD) needle proximal to the origin of the innominate artery. This temporarily caused complete occlusion of the aorta, but when the needle was removed the lumen was restored with a >60-80% reduction in diameter. Mice were sacrificed and tissues collected 1 month after the surgery.

Statistics. All data are expressed as means with error bars representing the standard error of the mean. Statistical calculations were performed using GraphPad Prism and SAS. Significance of differences were calculated by parametric student's t-test and non-parametric student's t-test with Mann-Whitney test where appropriate, when comparing differences between two groups. Significance of differences between multiple groups were calculated using two-way ANOVA with Tukey's correction. Chi-square test was used to compare significance of differences between different timepoints and different NAC treatment groups in supplemental tables 1, 2, 3, 6 and 7 with Fisher's exact test to calculate p values. A p value of less than 0.05 was considered significant.

Example 2—Results

The inventor previously showed that shear stress can activate latent TGF-β1 in vitro (Ahamed et al., 2008). Mice with a targeted deletion of Tgfb1 in their megakaryocytes and platelets are partially protected from developing cardiac hypertrophy, fibrosis, and systolic dysfunction in a pressure overload transverse aorta constriction model of AS (Meyer et al., 2012). Since high shear gradient is observed in AS patients and fibrosis is one of the major hallmarks of AS progression, the inventor hypothesized that platelet-derived TGF-β1 may contribute to AS progression. To test the role of platelet-derived TGF-β1 in AS progression, the inventor first needed to establish an aggressive and robust mouse model that simulates human AS, since only ~30% of elderly LDLR mice spontaneously develop AS in the present mouse model over a two-year period (Weiss et al., 2006). AS progression in LDLR mice can be accelerated by feeding them a Western Diet (WD) when they are adults (8 to 12 weeks of age) (Weiss et al., 2013; Miller et al., 2010, Wang et al., 2014), and the inventor hypothesized that a diet containing even higher cholesterol levels and commencing early, at 6 weeks of age, would further accelerate AS progression. Therefore, the inventor fed LDLR and control C57BL/6 (WT) mice a High Fat Diet (HFD) containing 6-fold higher cholesterol than WD, commencing at 6 weeks of age for up to 9 months (FIG. 5A).

The inventor found that LDLR mice fed the HFD had higher plasma cholesterol levels compared to LDLR mice on chow diet (CD), or to WT mice on HFD or CD (FIG. 5B). LDLR mice on HFD also displayed thickened aortic valve leaflets and increased total valve area (thickness) relative to WT mice on HFD, as revealed by histology and a new, modified ultrasound imaging view that improved visualization of early stage valve stenosis (FIGS. 1A-C). The inventor further assessed AS in each mouse cohort by measuring fractional valve opening, aortic valve (AV) peak velocity, and WSS across the valves. LDLR mice on HFD gradually developed AS over the 9 month period (FIG. 1D, FIG. 5C). The inventor found that over 90% of these mice were stenotic within 6 months (FIG. 5E). New echocardiography ultrasound imaging method resulted in high-resolution images that captured early evidence, and subtle differences in, valve stenosis, as an improvement over earlier models and methods, the inventor is are now able to demonstrate different stages of AS progression in mice. LDLR mice on HFD gradually developed AS in a time-dependent manner, mild at 1-2 months, moderate at 3-4 months, and severe by 5-6 months (FIG. 1E; FIG. 5C; Supplemental Tables 1-3), a classification of AS progression stages (mild, moderate, and severe AS) was well characterized in human, but not in mice. Thus, the inventor's AS model is robust in detecting subtle difference in AS progression.

Importantly, LDLR mice fed the HFD displayed more severe and accelerated AS compared to LDLR mice fed WD or CD. In contrast with LDLR mice fed the HFD, WT mice fed CD, WD, or the HFD did not develop AS (FIGS. 5D-F). Excessive collagen accumulation in the aortic valve is a hallmark of AS. Indeed, the inventor observed higher collagen levels in the aortic valves of LDLR mice on HFD compared to WT mice on HFD, as measured by immunohistochemistry and picrosirius staining (FIG. 1F). Thus, LDLR mice fed the HFD represent a robust preclinical model of AS. The inventor also examined AS progression in LDLR mice fed CD and WD and found that they developed varying degrees of AS and fibrosis as measured/evaluated by the new ultrasound techniques (data not shown).

Next, the inventor investigated potential roles for TGF-β1 and platelets in AS progression in LDLR mice fed HFD. LDLR mice on HFD had significantly higher plasma levels of TGF-β1 than WT mice, which directly correlated with WSS (FIGS. 6A-B) and was consistent with the inventor's previous findings (Wang et al., 2014). LDLR mice on HFD displayed higher TGF-β1-mediated signaling of p-Smad2 in valvular cells, mostly in the nuclei, than WT mice on HFD (FIGS. 6C-D). Further, immunostaining of whole mount aortic valves combined with scanning electron microscopic (SEM) imaging from LDLR mice on HFD revealed that activated platelets co-expressing CD41 and CD62P physically attached to valvular cells, which express high p-Smad2 in their nuclei (FIG. 1G). These findings implicate activated platelets inducing TGF-β1 signaling within valvular cells, resulting in AS progression.

To definitively assess the role of platelet-derived TGF-β1 in AS progression, the inventor then deleted Tgfb1 in platelets/megakaryocytes by crossing LDLR mice with Pf4Cre+Tgfb1f/f mice to generate Pf4Cre+Tgfb1f/f;Ldlr−/− Apob100/100 mice, designated TGF-β1$^{platelet-KO}$-LDLR, and their littermate controls Tgfb1f/f;Ldlr−/−Apob100/100, designated TGF-β1$^{flox}$-LDLR (FIGS. 7A-B; Supplemental Table 5). Pf4Cre+ expression in platelets led to reduced serum levels of TGF-β1 in Tgfb1f/+ and Tgfb1f/f mice, as expected (FIG. 7C). Further, TGF-β1$^{platelet-KO}$-LDLR mice displayed 80% lower levels of platelet TGF-β1 and 43% lower plasma TGF-β1 than TGF-β1flox-LDLR controls (FIGS. 2A-B). Mixed genotype mice (Pf4Cre+ mice heterozygous for either Tgfb1f or Ldlr- or with wild-type Apob) on HFD displayed similar fractional valve opening as WT mice on HFD (FIG. 7D), indicating that they did not develop severe AS. Mixed genotype mice also exhibited lower plasma cholesterol levels compared to both TGF-β1$^{platelet-KO}$-LDLR and TGF-β1$^{flox}$-LDLR mice (FIG. 7E), revealing that both alleles of Ldlr- and Apob100 are required to maintain high plasma levels of cholesterol.

The inventor found that TGF-β1$^{platelet-KO}$-LDLR mice fed the HFD were partially protected from developing AS, revealed by improved fractional valve opening, AV peak velocity, and WSS compared to TGF-β1$^{flox}$ (LDLR controls (FIG. 2C). Histological analyses showed reduced aortic valve thickening in TGF-β1$^{platelet-KO}$-LDLR mice compared to TGF-β1$^{flox}$-LDLR controls after 6 months on HFD (FIG. 2D; FIG. 7F). TGF-β1$^{platelet-KO}$-LDLR mice showed lower p-Smad2 levels in valvular cells compared to TGF-β1$^{flox}$-LDLR controls, indicating reduced TGF-β1 signaling activity (FIG. 2E, FIG. 7F). Moreover, p-Smad2 localized to the nucleus in valvular cells in TGF-β1$^{flox}$-LDLR mice, but to the cytoplasm of these cells in TGF-β1$^{platelet-KO}$-LDLR mice. However, activated platelets co-expressing CD41 and CD62P were adjacent to p-Smad2+ valvular cells in both TGF-β1$^{flox}$-LDLR and TGF-β1$^{platelet-KO}$-LDLR mice (FIG. 2F; FIG. 7G). These data suggest that platelet-derived TGF-β1 is a major contributor to AS progression, mediated via stimulation of TGF-β signaling in valvular cells. Mixed genotype mice did not develop AS compared to both TGF-β1$^{platelet-KO}$-LDLR and TGF-β1$^{flox}$-LDLR mice (data not shown), indicating that both alleles of Ldlr- and Apob100 are required for AS progression.

The inventor evaluated heart function parameters, and found significant deterioration of systolic heart function in LDLR mice compared to WT mice on HFD and to LDLR mice on CD (Supplemental Table 4). These findings suggest that the systemic high cholesterol levels and HFD are deleterious to heart function in LDLR. AS can also cause deterioration of heart functions by creating pressure overload to the heart, resulting in fibrosis and heart failure, as shown by the transverse aortic constriction model (Meyer et al., 2012).

To determine how platelet-derived TGF-β1 leads to increased collagen levels in aortic valves, the inventor performed multicolor immunofluorescence staining of valves to monitor phenotypic transformations and TGF-β signaling. While WT mice fed HFD displayed uniform expression of the mesenchymal marker, vimentin, in aortic valves, LDLR mice fed the HFD showed a subset of cells expressing higher levels of vimentin at the tip of the aortic valve facing the aorta—the region, which senses shear effects (FIG. 3A; FIG. 8A). These high vimentin-expressing cells at the tip of the valve also expressed p-Smad2 and the myofibroblast marker, α-SMA (FIG. 3B, FIGS. 8B-D). Valves from LDLR and WT mice on HFD stained for both vimentin and isolectinB4 (valvular endothelial cell (VEC) marker). However, the WT valve expressed isolectinB4 uniformly in the endothelial lining, whereas isolectinB4 cells in the LDLR valve migrated towards the inner layers of the valve (FIG. 3C). Aortic valves in LDLR mice displayed a dramatic increase in collagen expression around vimentin-positive cells (FIG. 3D) compared to WT mice fed the HFD.

Figure 8E:
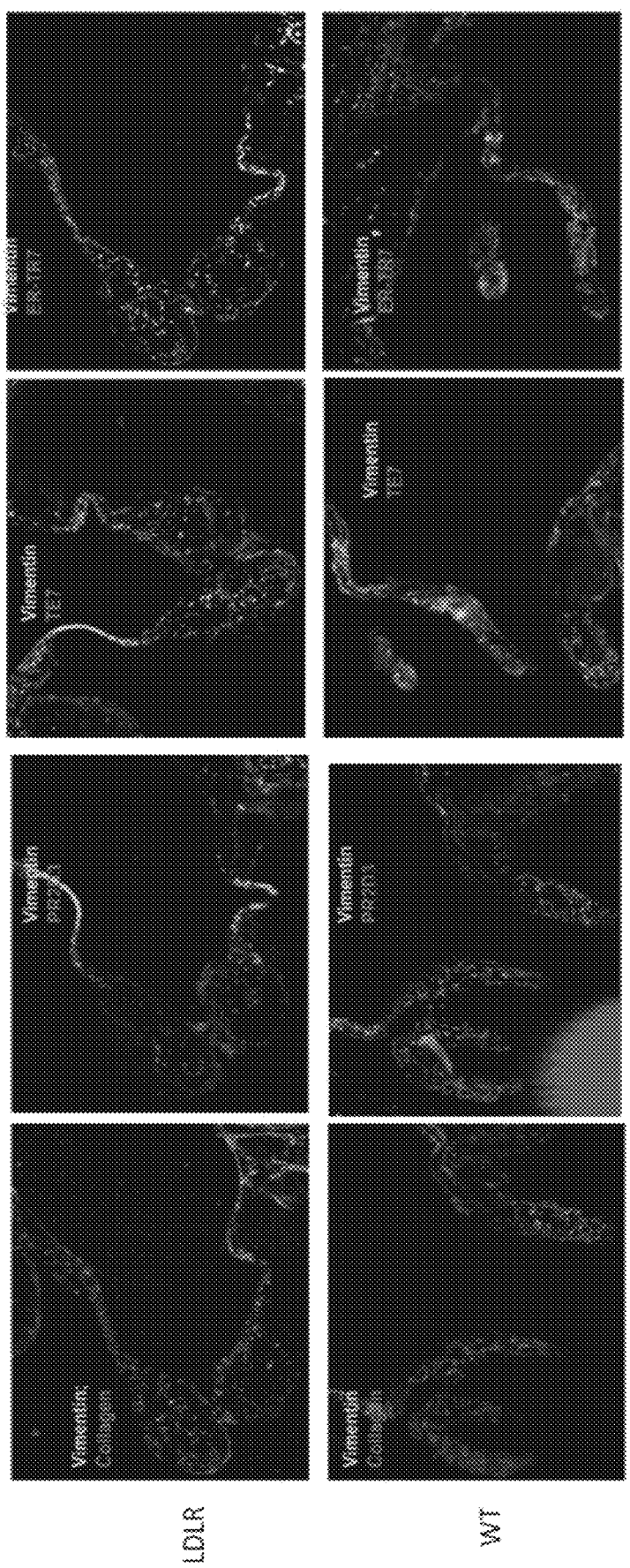

Aortic valves from LDLR mice on HFD also displayed higher levels of other myofibroblast and fibroblast markers, including PR2D3, TE7, and ER-TR7, than those from WT mice on HFD (FIG. 8E). The inventor also observed co-localization of isolectinB4, vimentin, and α-SMA in the AS valves of TGF-β1$^{flox}$-LDLR mice on HFD, whereas little co-localization was observed in the valves of TGF-β1$^{platelet-KO}$-LDLR mice on HFD (FIG. 3E). These data suggest that platelet-derived TGF-β signaling in VECs triggers their transformation into collagen-producing myofibroblasts (unpublished data).

Figure 8F:
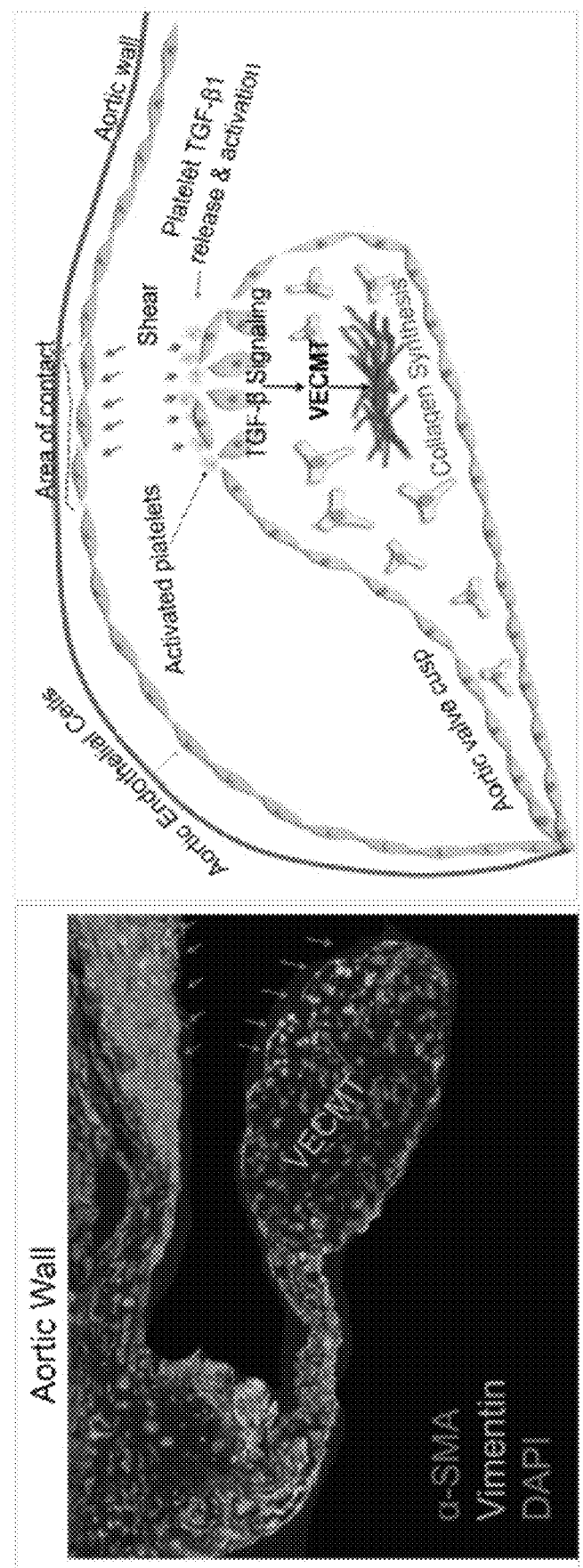

To further investigate this hypothesis, the inventor evaluated valves in a different model of AS using Tie2-Cre; tdTomato reporter mice, which mark endothelial lineage cells. He subjected Tie2-Cre;tdTomato mice to high-shear ascending aortic constriction (AAC) to simulate very high mixed shear conditions (laminar/turbulent/oscillatory/vortexes), and hypothesized that VECs facing the aortic side sense turbulent/oscillatory shear, similar to what occurs in AS conditions. AAC induces high shear across the valves, but it also induces oscillatory shear on the VECs. IsolectinB4, vimentin, and α-SMA staining showed the outer layer VECs express all three markers, suggesting valvular endothelial cell-to-mesenchymal transition (VECMT) (FIG. 3F; FIG. 8F). Lineage tracing of the VEC through tdTomato expression in AAC mice showed a subset of VECs also express vimentin (FIG. 3F). These data provide further support that VECs transform into myofibroblasts under high shear models such as AAC and AS, and suggest that platelet-derived TGF-β1 activated by shear stress transforms VECs into collagen-producing myofibroblasts. Although the inventor previously showed high shear force generated in vivo in two mouse models, FeCl$_3$-induced carotic artery thrombosis, and transverse aortic constriction (TAC) resulting in local and systemic increase in active and total TGF-β1 levels (Ahamed et al., 2008; Meyer et al., 2012), his current AAC model is much more aggressive and robust in terms of high shear generated in the ascending aorta and creating a turbulent flow near and around the aortic valve leaflets. This model develops quickly and can potentially be used for preclinical evaluation of drugs for EndoMT/VECMT/EMT phenotypes mediated by shear and TGF-β1-mediated signaling in vivo. This model also leads to massive cardiac fibrosis and deterioration of heart functions much more aggressively and quickly (a manuscript under preparation) than the TAC model the inventors published previously (Meyer et al., 2012).

The data reveal that platelet-derived TGF-β1 directly contributes to AS development. The inventor previously showed that N-acetylcysteine (NAC) inhibited shear-dependent activation of latent TGF-β1 released from platelets in vitro (Ahamed et al., 2008). Therefore, the inventor hypothesized that NAC treatment would inhibit AS progression in LDLR mice on HFD by blocking shear-dependent platelet TGF-β1 activation in vivo. To verify that NAC treatment inhibits the activation of TGF-β1 in vivo, the inventor isolated platelet-rich plasma (PRP) from mice treated or untreated with NAC and subjected the PRP to shear force of 1,800 s$^{-1}$ in a custom-made cone and plate shear device for 2 hours. Indeed, TGF-β1 activation was much lower in PRP from NAC-treated mice than control mice (FIG. 4A).

Figure 9:
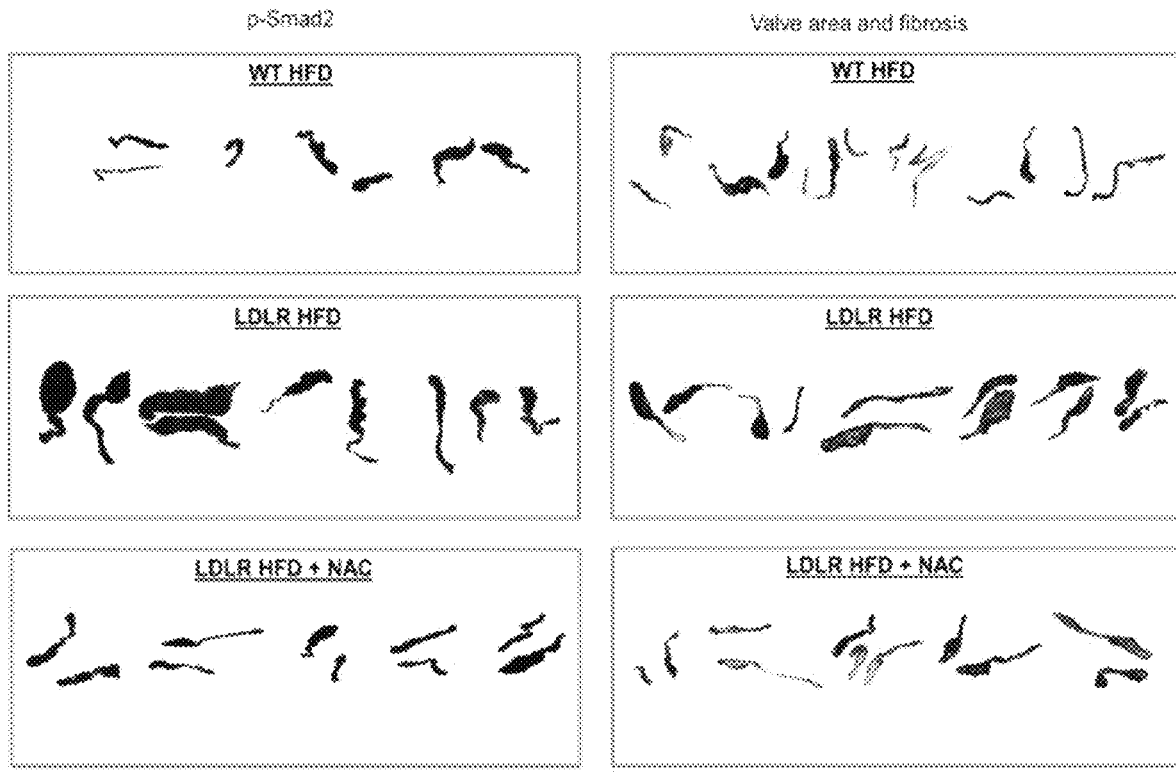
FIG. 9. Representative images of p-Smad2 and picrosirius red-stained aortic valves from WT and LDLR mice after 6 months of HFD, with or without NAC treatment.

The inventor treated LDLR mice on HFD with a pharmacological dose of NAC commencing at different stages of AS (FIG. 4B). He found that LDLR mice on HFD and treated with NAC from months 3-5 (moderate AS) and months 5-6 (severe AS) displayed an improved fractional valve opening and WSS compared to untreated control mice (FIG. 4C; Supplemental Tables 6-7). Thus, NAC treatment halted the progression of AS at various stages of AS progression. Combining the mice treated at 3-5 and 5-6 months, the inventor observed reduced p-Smad2 staining, aortic valve area, and fibrosis in NAC-treated LDLR mice on HFD compared to untreated control mice (FIG. 4D; FIG. 9), further supporting decreased TGF-β1 signaling and inhibited AS progression in NAC-treated mice. To confirm that NAC improves the valve phenotype by specifically inhibiting platelet-derived TGF-β1 activation, the inventor treated TGF-β1$^{platelet-KO}$-LDLR mice on HFD with NAC. He observed little to no further reduction of AS progression (FIG. 4E), indicating that NAC attenuates AS primarily by blocking platelet-derived TGF-β1 activation.

This is very interesting finding, as only the short-term NAC was effectively tested in moderate and severe AS stages. Thus, further studies are needed to test its efficacy in mild and even more symptomatic AS as well as mixed valvular diseases with aortic regurgitation (AR), and other valvular disease. Short-term treatment from 2-3 months also halted mild to moderate AS progression (data not shown). Interestingly, long-term NAC treatment (1-6 months) lead to adverse effects, including deterioration of heart function and increased atherosclerotic plaque with very little to no effect on AS (data not shown). These data indicate that NAC blocks AS by inhibiting shear-induced TGF-β1 activation, thus inhibiting initiation of TGF-β signaling in VECs and/or other valvular cells, whereas long-term NAC treatment may have some unknown side effects. Further studies are needed to evaluate the deleterious effect of NAC on cardiac functions. Recent preliminary data obtained by the inventor shows that blocking TGF-β receptor-mediated signaling P-Smad2 using a very low concentration of galunisertive (LY2157299) also halted AS progression in LDLR mice and inhibited cardiac fibrosis-induced by ascending aortic contriction in WT C57Bl/6 mice (unpublished data). Taken together, these data support the conclusion that blocking TGF-β1 activation and/or TGF-β receptor-mediated Smad signaling can potentially prevent/mitigate fibrotic disease, including AS and cardiac fibrosis.

Example 3—Discussion

Here, the inventor has shown that platelet-derived TGF-β1 directly contributes to AS progression in a robust preclinical mouse model of AS, and that pharmacologically or genetically blocking platelet-derived TGF-β1 activity halts AS progression. NAC is a safe, FDA-approved drug used to treat many different conditions (Smilkstein et al., 1988; Marenzi et al., 2006), and its use overcomes the failure of other clinical trials for anti-TGF-β1 therapy due to the pleiotropic nature of TGF-β1 in regulating many physiological functions, including immune function. Moreover, NAC also partially inhibits shear-dependent activation of TGF-β1, presumably by blocking thiol disulfide exchange, a mechanism that has been proposed to contribute to shear-dependent TGF-β1 activation (Ahamed et al., 2008). Thus, compounds such as NAC and/or other thiol-reactive molecules or proteins/peptides may play a regulatory role in the balance between biological and pathological functions of TGF-β1 in which excess TGF-β1 generation may cause pathologic fibrosis.

This work also developed new preclinical tools/models to study AS. The inventor's discovery that feeding LDLR mice a HFD accelerates AS progression will reduce the time required for preclinical drug evaluation. In addition, the inventor established a method to characterize AS by obtaining ultrasound images using a modified stable view of aortic valves, which allows precise measurement of valve opening and blood flow velocity across the valves. This method detects even mild to moderate stenosis at early stages of AS for diagnostic and preclinical purposes. The varying degrees of AS severity (mild, moderate or severe) in humans are well-characterized (Otto, 2006; Baumgartner et al., 2009; Vahanian et al., 2007; Zoghbi et al., 2003), but similar guidelines for stenosis classification in mice are lacking. The inventor's analysis of valve thickness measured by ultrasound corresponds with histological and immunofluorescence evaluation, demonstrating the robustness of the technique. Based on this approach, the inventor proposes a new classification system for different stages of AS (mild, moderate and severe) in mice (Supplemental Tables 1-3). This approach could be used to evaluate target genes responsible using genetically-engineered mice for AS development and preclinical screening of drugs/compounds/antibodies/peptides.

This study shows, for the first time to the inventor's knowledge, that activated platelets surround valve cells and stimulate TGF-β1 signaling Bouchareb et al. (2018) recently reported that activated platelets promote osteogenic program in calcific aortic valve stenosis, complements our results showing activated platelets are physically associated with VECs driving AS pathology. Valvular cells near activated platelets have higher expression and nuclear translocation of p-Smad2 in mice with AS, suggesting that TGF-β1 is released from platelets locally and most likely activated by shear. These data suggest a new concept: that local concentrated TGF-β1 release from platelets exerts a more potent signaling effect on VECs than systemic TGF-β1 diluted in circulatory blood. Fibrosis is a hallmark of AS, and endothelial cell-to-mesenchymal transition has been shown to play a key role in the development of cardiac valves during embryogenesis (Lincoln et al., 2004; de Lange et al., 2004; Rivera-Feliciano et al., 2006; Snarr et al., 2008). These data show that a subset of VECs, apparently in the region of the valve, which senses possibly harmful oscillatory/disturbed/turbulent, shear, are migrating inwards, undergoing VECMT due to elevated TGF-β1 signaling induced by TGF-β1 released from activated platelets attached to the VECs, giving rise to collagen-producing myofibroblasts and causing AS (depicted in FIG. 8F). To the inventor's knowledge, there has been no in vivo study to date showing this mechanism in AS. Finally, the inventor provides evidence that blocking shear-dependent activation of platelet TGF-β1 by thiol-reactive agents, such as NAC, might provide therapeutic relief in AS progression, which should be tested in other preclinical animal models and clinical trials for AS patients.

AS is a fibrocacific disease involving both fibrosis and calcification of the valves, thus, and the inventor predicts the potential role of platelet TGF-β1 in calcification, which will also be tested experimentally. In addition to chemicals similar to NAC or other thiol-reactive compounds, biologics, including antibodies and peptides, will also be evaluated for their ability to block AS as well as other fibrotic disorders. Moreover, the new ultrasound technique developed by the inventor is unique for viewing aortic valves clearly, and so can be used to evaluate percentages and stages of AS progression in genetically-engineered or LDLR mice fed with normal chow or high-fat diets containing different concentrations of total cholesterol.

The inventors will test other related thiol-reactive compounds such as NAC in addition to OKN007 (patented separately for the treatment of other diseases), which reacts with thiols to inhibit TGF-β activation in vivo. They will characterize AS and cardiac fibrosis using our modified method of ultrasound imaging as well as immunohistological characterizations of tissue phenotypes and correlate with disease progression.

SUPPLEMENTAL TABLE 1

Penetrance Data for Fractional Valve Opening

| Time Point (Months) | 0-1 | 1-2 | 3-4 | 5-6 | 7-9 |
| --- | --- | --- | --- | --- | --- |
| Total (n) | 14 | 16 | 34 | 28 | 8 |
| No Stenosis >0.85 | 7 (50%) | 9 (56%) | 11 (32%) | 0 (0%) | 0 (0%) |
| Mild Stenosis 0.75-0.85 | 6 (43%) | 6 (38%) | 7 (21%) | 1 (4%) | 0 (0%) |
| Moderate Stenosis 0.6-0.75 | 0 (0%) | 1 (6%) | 10 (29%) | 12 (43%) | 0 (0%) |
| Severe Stenosis <0.6 | 1 (7%) | 0 (0%) | 6 (18%) | 15 (53%) | 8 (100%) |

LDLR mice on HFD develop aortic stenosis within 6 months. Penetrance of aortic stenosis in LDLR mice on HFD at various time points from initiation of HFD as measured by fractional valve opening. Significance of differences between the various timepoints was calculated by Chi Square analysis and Fisher's exact test was used to calculate p value. p value was found to be less than 0.0001, indicating significant differences between the groups.

SUPPLEMENTAL TABLE 2

Penetrance Data for Wall Shear Stress

| Time Point (Months) | 0-1 | 1-2 | 3-4 | 5-6 | 7-9 |
|---|---|---|---|---|---|
| Total (n) | 14 | 16 | 34 | 28 | 8 |
| No Stenosis <350 dyn/cm$^2$ | 7 (50%) | 9 (56%) | 11 (32%) | 0 (0%) | 0 (0%) |
| Mild Stenosis 350-525 dyn/cm$^2$ | 6 (43%) | 6 (38%) | 7 (21%) | 8 (28%) | 0 (0%) |
| Moderate Stenosis 525-700 dyn/cm$^2$ | 0 (0%) | 1 (6%) | 10 (29%) | 5 (18%) | 0 (0%) |
| Severe Stenosis >700 dyn/cm$^2$ | 1 (7%) | 0 (0%) | 6 (18%) | 15 (54%) | 8 (100%) |

LDLR mice on HFD develop aortic stenosis within 6 months. Penetrance of aortic stenosis in LDLR mice on HFD at various time points from initiation of HFD as measured by wall shear stress across the valve. Significance of differences between the various timepoints was calculated by Chi Square analysis and Fisher's exact test was used to calculate p value. p value was found to be less than 0.0001, indicating significant differences between the groups.

SUPPLEMENTAL TABLE 3

Penetrance Data for Aortic Valve Peak Velocity

| Time Point (Months) | 0-1 | 1-2 | 3-4 | 5-6 | 7-9 |
|---|---|---|---|---|---|
| Total (n) | 14 | 18 | 40 | 25 | 8 |
| No Stenosis <1200 mm/s | 9 (64) | 14 (78%) | 8 (2%) | 2 (8%) | 0 (0%) |
| Mild Stenosis 1200-1400 mm/s | 3 (22%) | 1 (5%) | 17 (42%) | 6 (24%) | 0 (0%) |
| Moderate Stenosis 1400-1600 mm/s | 0 (0%) | 3 (17%) | 6 (15%) | 10 (40%) | 0 (0%) |
| Severe Stenosis >1600 mm/s | 2 (14%) | 0 (0%) | 9 (23%) | 7 (28%) | 8 (100%) |

LDLR mice on HFD develop aortic stenosis within 6 months. Penetrance of aortic stenosis in LDLR mice on HFD at various time points from initiation of HFD as measured by aortic valve peak velocity. Significance of differences between the various timepoints was calculated by Chi Square analysis and Fisher's exact test was used to calculate p value. p value was found to be less than 0.0001, indicating significant differences between the groups.

SUPPLEMENTAL TABLE 4

Heart Function Data

| | WT CD | WT HFD | LDLR CD | LDLR HFD | Littermate Controls | Final Genotype |
|---|---|---|---|---|---|---|
| EF (%) | 72.58 ± 2.043 | 68.73 ± 1.808 | 63.46 ± 3.376 | 54.92 ± 1.187*$ | 55.1 ± 2.077* | 52.47 ± 1.928*$ |
| FS (%) | 41.1 ± 1.675 | 37.95 ± 1.424 | 34.68 ± 2.458 | 30.57 ± 1.112* | 27.54 ± 1.258* | 26.83 ± 1.243*$ |
| CO (ml/min) | 28.84 ± 1.369 | 17.52 ± 1.546# | 29.29 ± 2.831 | 21.4 ± 0.6339*$ | 20.95 ± 1.632$ | 19.94 ± 0.7967$ |
| SV (μl) | 62.24 ± 3.415 | 37.93 ± 2.024# | 57.93 ± 5.917 | 44.37 ± 1.196*$ | 43.24 ± 3.085 | 41.1 ± 1.458$ |
| Heart Rate (BPM) | 442.6 ± 28.18 | 490.2 ± 20.28 | 510.2 ± 11.73# | 483.1 ± 5.96$ | 483.3 ± 13.11 | 484.7 ± 7.125 |
| LVID; d (mm) | 1.121 0.04352 | 0.9844 0.03207# | 0.9546 0.1259# | 0.9055 0.0352 | 4.128 0.1183*&$ | 4.223 0.09959*&$ |
| LVID: s (mm) | 1.79 0.08908 | 1.519 0.05499# | 1.28 0.0437# | 1.369 0.04445 | 2.905 0.1063*&$ | 3.093 0.1193*&$ |
| LV Vol; d (μl) | 59.44 4.924 | 55.74 9.158 | 80.68 8.826 | 78.21 3.131* | 76.1 5.118 | 79.8 4.245* |
| LV Vol; s (μl) | 17 2.189 | 23.05 3.982 | 33.49 4.861 | 35.22 2.374* | 32.87 2.9 | 38.7 3.288* |

*significant (p < 0.05) compared to WT HFD
$significant (p < 0.05) compared to LDLR CD
&significant (p < 0.05) compared to LDLR HFD
significant (p < 0.05) compared to WT CD Systolic heart function parameters measured by echocardiography in WT, LDLR, TGF-β1flox-LDLR control (littermate control), and TGF-β1platelet-KO-LDLR mice fed with CD or HFD, with or without NAC treatment as indicated.

SUPPLEMENTAL TABLE 5

PCR genotyping for TGF-β1platelet-KO-LDLR and their littermate controls

| Total number of pups from breeder pair | Pup Genotypes | Number w/ Genotype | Observed % | Expected # | Expected % | Possible Genotypes From Crossing | Number of Litters |
|---|---|---|---|---|---|---|---|
| | PF4Cre+; LDLR+/−; ApoB−/−; TGFbf/f | 1 | 5 | 1 | 2.34 | 81 | |
| | PF4Cre+; LDLR+/+; ApoB+/−; TGFb+/+ | 1 | 5 | 1 | 3.51 | 81 | |
| | PF4Cre+; LDLR+/+; ApoB+/−; TGFb+/f | 4 | 20 | 1 | 7.03 | 81 | |
| 16 | PF4Cre+/+; LDLR−/−; ApoB−/−; TGFbf/f | 1 | 6.3 | 1 | 1.56 | 54 | 2 |
| | PF4Cre+/+; LDLR+/+; ApoB+/−; TGFb+/f | 1 | 6.3 | 2 | 9.38 | 54 | |
| | PF4Cre+/+; LDLR−/−; ApoB+/−; TGFb+/+ | 1 | 6.3 | 1 | 4.68 | 54 | |
| | PF4Cre+/+; LDLR+/−; ApoB+/−; TGFb+/+ | 1 | 6.3 | 2 | 9.38 | 54 | |
| | PF4Cre+/+; LDLR+/−; ApoB+/−; TGFb+/f | 7 | 43.8 | 3 | 18.76 | 54 | |
| | PF4Cre+/+; LDLR+/−; ApoB+/−; TGFbf/f | 1 | 6.3 | 2 | 9.38 | 54 | |
| | PF4Cre+/+; LDLR+/−; ApoB+/+; TGFb+/f | 1 | 6.3 | 1 | 6.26 | 54 | |
| | PF4Cre+/+; LDLR+/+; ApoB+/−; TGFb+/+ | 1 | 6.3 | 1 | 3.12 | 54 | |
| | PF4Cre+/+; LDLR+/+; ApoB+/−; TGFb+/f | 1 | 6.3 | 2 | 9.38 | 54 | |
| 19 | PF4Cre+; LDLR+/−; ApoB+/−; TGFb+/f | 8 | 42.1 | 3 | 14.07 | 36 | 4 |
| | PF4Cre+; LDLR+/−; ApoB+/−; TGFbf/f | 6 | 31.6 | 3 | 14.07 | 36 | |
| | PF4Cre−/−; LDLR+/−; ApoB+/−; TGFb+/f | 3 | 15.8 | 1 | 4.69 | 36 | |
| | PF4Cre−/−; LDLR+/−; ApoB+/−; TGFbf/f | 2 | 10.5 | 1 | 4.69 | 36 | |
| 15 | PF4Cre−/−; LDLR−/−; ApoB+/−; TGFb+/f | 3 | 20.0 | 2 | 12.5 | 6 | 2 |
| | PF4Cre−/−; LDLR−/−; ApoB+/−; TGFbf/f | 5 | 33.3 | 2 | 12.5 | 6 | |
| | PF4Cre+; LDLR−/−; ApoB+/−; TGFb+/f | 4 | 26.7 | 6 | 37.5 | 6 | |
| | PF4Cre+; LDLR−/−; ApoB+/−; TGFbf/f | 3 | 20.0 | 6 | 37.5 | 6 | |
| 14 | PF4Cre+/+; LDLR+/+; ApoB+/−; TGFbf/f | 2 | 14.3 | 3 | 18.75 | 9 | 9 |
| | PF4Cre+/+; LDLR−/−; ApoB+/−; TGFbf/f | 4 | 28.6 | 3 | 18.75 | 9 | |
| | PF4Cre+/+; LDLR+/−; ApoB+/−; TGFbf/f | 6 | 42.9 | 5 | 37.5 | 9 | |
| | PF4Cre+/+; LDLR−/−; ApoB−/−; TGFbf/f | 2 | 14.3 | 1 | 6.25 | 9 | |
| 22 | PF4Cre+/−; LDLR−/−; ApoB+/−; TGFbf/f | 19 | 86.4 | 17 | 75 | 3 | 5 |
| | PF4Cre−/−; LDLR−/−; ApoB+/−; TGFbf/f | 3 | 13.6 | 6 | 25 | 3 | |
| 24 | PF4Cre+/−; LDLR−/−; ApoB+/−; TGFbf/f | 18 | 75 | 18 | 75 | 3 | 7 |
| | PF4Cre−/−; LDLR−/−; ApoB+/−; TGFbf/f | 6 | 25 | 6 | 25 | 3 | |
| 3 | PF4Cre+/−; LDLR−/−; ApoB+/−; TGFbf/f | 2 | 66.7 | 2 | 75 | 3 | 1 |
| | PF4Cre−/−; LDLR−/−; ApoB+/−; TGFbf/f | 1 | 33.3 | 1 | 25 | 3 | |
| 5 | PF4Cre+/+; LDLR−/−; ApoB+/−; TGFbf/f | 5 | 100 | 5 | 100 | 1 | 1 |
| 6 | PF4Cre−/−; LDLR−/−; ApoB+/−; TGFbf/f | 1 | 16.7 | 2 | 25 | 3 | 1 |
| | PF4Cre−/−; LDLR−/−; ApoB+/−; TGFbf/f | 5 | 83.3 | 5 | 75 | 3 | |
| 25 | PF4Cre+/−; LDLR−/−; ApoB+/−; TGFbf/f | 22 | 88 | 19 | 75 | 3 | 6 |
| | PF4Cre−/−; LDLR−/−; ApoB+/−; TGFbf/f | 3 | 12 | 6 | 25 | 3 | |
| 8 | PF4Cre+/+; LDLR−/−; ApoB+/−; TGFbf/f | 8 | 100 | 8 | 100 | 1 | 1 |
| 8 | PF4Cre+/+; LDLR−/−; ApoB+/−; TGFbf/f | 8 | 100 | 8 | 100 | 1 | 1 |

SUPPLEMENTAL TABLE 5-continued

PCR genotyping for TGF-β1platelet-KO-LDLR and their littermate controls

| Total number of pups from breeder pair | Pup Genotypes | Number w/ Genotype | Observed % | Expected # | Expected % | Possible Genotypes From Crossing | Number of Litters |
|---|---|---|---|---|---|---|---|
| 3 | PF4Cre+/−; LDLR−/−; ApoB+/−; TGFbf/f | 3 | 100 | 3 | 100 | 1 | 1 |

SUPPLEMENTAL TABLE 6

Penetrance Data for Fractional Valve Opening

| Time Point (Months) | LDLR HFD | LDLR HFD + NAC (2-5 Months) | LDLR HFD + NAC (3-5 Months) | LDLR HFD + NAC (5-6 Months) |
|---|---|---|---|---|
| Total (n) | 28 | 8 | 11 | 7 |
| No Stenosis >0.85 | 0 (0%) | 0 (0%) | 0 (0%) | 0 (0%) |
| Mild Stenosis 0.75-0.85 | 1 (4%) | 1 (12%) | 2 (16%) | 3 (43%) |
| Moderate Stenosis 0.6-0.75 | 12 (43%) | 2 (25%) | 7 (64%) | 4 (57%) |
| Severe Stenosis <0.6 | 15 (53%) | 5 (53%) | 2 (18%) | 0 (0%) |

NAC treatment attenuates aortic stenosis progression. Penetrance of aortic stenosis in LDLR mice on HFD with various NAC treatments as measured by fractional valve opening. Significance of differences between the various timepoints was calculated by Chi Square analysis and Fisher's exact test was used to calculate p value. p value was found to be less than 0.0001, indicating significant differences between the groups.

SUPPLEMENTAL TABLE 7

Penetrance Data for Wall Shear Stress

| Time Point (Months) | LDLR HFD | LDLR HFD + NAC (2-5 Months) | LDLR HFD + NAC (3-5 Months) | LDLR HFD + NAC (5-6 Months) |
|---|---|---|---|---|
| Total (n) | 28 | 8 | 11 | 7 |
| No Stenosis <350 dyn/cm$^2$ | 0 (0%) | 0 (0%) | 0 (0%) | 0 (0%) |
| Mild Stenosis 350-525 dyn/cm$^2$ | 6 (28%) | 0 (0%) | 4 (36%) | 3 (43%) |
| Moderate Stenosis 525-700 dyn/cm$^2$ | 5 (18%) | 3 (37%) | 5 (46%) | 4 (57%) |
| Severe Stenosis >700 dyn/cm$^2$ | 15 (54%) | 6 (63%) | 2 (18%) | 0 (0%) |

NAC treatment attenuates aortic stenosis progression. Penetrance of aortic stenosis in LDLR mice on HFD with various NAC treatments as measured by wall shear stress. Significance of differences between the various timepoints was calculated by Chi Square analysis and Fisher's exact test was used to calculate p value. p value was found to be less than 0.0001, indicating significant differences between the groups.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods, and in the steps or in the sequence of steps of the methods described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

V. REFERENCES

The following references, to the extent that they provide exemplary procedural or other details supplementary to those set forth herein, are specifically incorporated herein by reference.

Ahamed et al., *Blood* 112, 3650-3660, 2008.
Assoian et al., *J Biol Chem* 258, 7155-7160, 1983.
Baumgartner et al., *J Am Soc Echocardiogr* 22, 1-23; quiz 101-102, 2009.
Bouchareb et al., *J Mol Cell Cardiol* 82, 104-115, 2015.
Bouchareb et al. (*Eur Heart J.*, doi: 10.1093/eurheartj/ehy696, 2018
Chu et al., *Arterioscler Thromb Vasc Biol* 33, 523-532, 2013.
Chu et al., *Arterioscler Thromb Vasc Biol* 36, 466-474, 2016.
de Lange et al., *Circ Res* 95, 645-654, 2004.
Gao et al., *Curr Protoc Mouse Biol* 1, 71-83, 2011.
Gould et al., *Circ Res* 113, 186-197, 2013.
Hajj et al., *Arterioscler Thromb Vasc Biol* 35, 1653-1662, 2015.
Jung et al., *J Nucl Med* 56, 933-938, 2015.
Le Quang et al., *Arterioscler Thromb Vasc Biol* 34, 2283-2291, 2014.
Lincoln et al., *Dev Dyn* 230, 239-250, 2004.
Lindman et al., *Nat Rev Dis Primers* 2, 16006, 2016.
Marenzi et al., *N Engl J Med* 354, 2773-2782, 2006.
Meyer et al., *Blood* 119, 1064-1074, 2012.
Miller et al., *Arterioscler Thromb Vasc Biol* 30, 2482-2486, 2010.
Miller et al., *Circulation* 119, 2693-2701, 2009.
Otto et al., *J Am Coll Cardiol* 47, 2141-2151, 2006.

Pistner et al., *J Vis Exp*, 2010.
Rajamannan et al., *Circulation* 124, 1783-1791, 2011.
Remington's Pharmaceutical Sciences, 15$^{th}$ ed., 1035-1038 and 1570-1580, Mack Publishing Company, PA, 1980.
Smilkstein et al., *N Engl J Med* 319, 1557-1562, 1988.
Snarr et al., *Dev Dyn* 237, 2804-2819, 2008.
Sung et al., *Arterioscler Thromb Vasc Biol* 36, 1627-1637, 2016.
Vahanian et al., *Eur Heart J* 28, 230-268, 2007.
Villar et al., *PLoS One* 4, e8476, 2009.
Wang et al., *Arterioscler Thromb Vasc Biol* 34, 1924-1932, 2014.
Weiss et al., *Circulation* 114, 2065-2069, 2006.
Weiss et al., *PLoS One* 8, e65201, 2013.
Yeang et al., *Cardiovasc Drugs Ther* 30, 75-85, 2016.
Zoghbi et al., *J Am Soc Echocardiogr* 16, 777-802, 2003.

What is claimed is:

1. A method of treating aortic valve stenosis in a human subject comprising administering to said subject N-acetylecysteine (NAC) at about 0.01 to 4 g of NAC per kg per day.

2. The method of claim 1, wherein administering comprises subcutaneous administration, intravenous administration, or administration by inhalation.

3. The method of claim 1, wherein administering comprises oral administration.

4. The method of claim 1, wherein the aortic valve stenosis is mild.

5. The method of claim 1, wherein the aortic valve stenosis is moderate.

6. The method of claim 3, wherein the aortic valve stenosis is severe.

7. The method of claim 1, wherein said aortic valve stenosis is caused by age-related progressive fibrosis, calcification of a congenital bicuspid aortic valve, unicaspid valves with unknown causes, acute rheumatic fever, post-inflammatory responses, Fabry disease, systemic lupus erythematosus, Paget disease, high blood uric acid levels, infection, mixed aortic valve diseases, including aortic regurgitation and aortic valve fusion after LVAD implantation in heart failure patients, and hypertension-induced cardiac pressure overload.

8. The method of claim 1, further comprising treating said subject with a statin or other cholesterol reducing agent, an anti-diabetic medication, an anti-hypertensive agent, a thiol-reactive compound, an anti-oxidant, or an anti-inflammatory agent.

9. The method of claim 1, further comprising treating said subject with aortic valve repair, reconstruction or replacement surgically or percutaneously (TAVR/TAVI).

10. The method of claim 1, wherein treating comprises slowing, mitigating or preventing the progression of said aortic valve stenosis.

11. The method of claim 1, wherein NAC is administered daily, every other day, weekly, biweekly or monthly.

12. The method of claim 1, wherein administration of NAC results in one or more of blocking platelet reactivity, blocking release and activation of factors responsible for inducing aortic stenosis and organ fibrosis and hypercoagulable states.

13. The method of claim 1, further comprising measuring platelet activation and release of factors, activation and their signaling components as biomarkers for predicting different stages of aortic stenosis or procoagulant stages in humans where high shear force (hemodynamix of blood flow pattern change in the vasculature, mechanical stain in tissues/cells) is observed.

14. The method of claim 1, further comprising evaluating disease progression concurrent with time of treatment and the stage of disease.

15. The method of claim 8, wherein the statin or other cholesterol reducing agent is a PCSK9 inhibitor, the anti-diabetic medication is metformin, the anti-hypertensive agent is a beta-blocker, a calcium blocker, a nitrate, digoxin, a diuretic, or an ACE inhibitor, the thiol-reactive compound is OKN007, the anti-oxidant is an Nrf2/HO-1 enhancer, a ROS scavenger, and/or the anti-inflammatory agent is anti-IL1β or anti-TNFα.

16. The method of claim 13, wherein measuring platelet activation and release of factors comprises measuring TGF-β1.

17. The method of claim 14, wherein evaluating comprises assessing pathological fibrosis and/or calcification.

18. The method of claim 12, further comprising wherein administration of an inhibitor of TGF-β activation and signaling.

* * * * *